(12) United States Patent
Peters et al.

(10) Patent No.: US 8,058,798 B2
(45) Date of Patent: Nov. 15, 2011

(54) EMISSIVE METAL COMPLEXES

(75) Inventors: Jonas C. Peters, Brookline, MA (US); Kenneth J. Lotito, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/580,844

(22) Filed: Oct. 16, 2009

(65) Prior Publication Data

US 2011/0089818 A1 Apr. 21, 2011

(51) Int. Cl.
*H01J 1/62* (2006.01)
*C07F 1/08* (2006.01)
*C07F 15/00* (2006.01)

(52) U.S. Cl. ............ 313/504; 556/21; 556/110; 548/402

(58) Field of Classification Search ............... 556/21, 556/110; 548/402; 313/504
See application file for complete search history.

(56) References Cited

OTHER PUBLICATIONS

Uson et al. Polyhedron 3(4), 1984, 497-501. Abstract Only. (One page).*
Vicente et al. J. Chem. Soc. Dalton Trans. 1995, pp. 1251-1254.*
STN Structure search of 002/09/2011 (40 pages).*
STN Structure search of 002/08/2011 (40 pages).*
Balzani, V.; Juris, A.; Venturi, M.; Campagna, S.; Serroni, S. *Chem. Rev.* 1996, 96, 759-833.
Becke, A. D. *J. Chem. Phys.* 1993, 98, 5648-5652.
Blue, E. D.; Davis, A.; Conner, D.; Gunnoe, T. B.; Boyle, P. D.; White, P. S. *J. Am. Chem. Soc.* 2003, 125, 9435-9441.
Cline, E. D.; Kraml, C. M.; Byrne, N.; Ho, D. M.; Qin, Q.; Coughlin, F. J.; Bernhard, S.; Pascal, R. A. *Inorg. Chem.* 2008, 47, 10378-10388.
Cuttell, D. G.; Kuang, S. -M.; Fanwick, P. E.; McMillin, D. R.; Walton, R. A. *J. Am. Chem. Soc.* 2002, 124, 6-7.
Dawson, W. R.; Windsor, M. W. *J. Phys. Chem.* 1968, 72, 3251-3260.
Demas, J. N.; Crosby, G. A. *J. Phys. Chem.* 1971, 75, 991-1024.
Eriksson, H.; Hkansson, M. *Organometallics*, 1997, 16, 4243-4244.
Fan, L.; Yang, L.; Guo, C.; Foxman, B. M.; Ozerov, O. V. *Organometallics* 2004, 23, 4778-4787.
Ford, P. C.; Cariati, E.; Bourassa, J. *Chem. Rev.* 1999, 99, 3625-3627.
Goj, L. A.; Blue, E. D.; Munro-Leighton, C.; Gunnoe, T. B.; Petersen, J. L. *Inorg. Chem.*, 2005, 44, 8647-8649.
Goldsmith, J. I.; Hudson, W. R.; Lowry, M. S.; Anderson, T. H.; Berhard, S. *J. Am. Chem. Soc.* 2005, 127, 7502-7510.
Harkins, S. B.; Mankad, N. P.; Miller, A. J. M.; Szilagyi, R. K.; Peters, J. C. *J. Am. Chem. Soc.* 2008, 130, 3478-3485.
Horvath, O. *Coord. Chem. Rev.* 1994, 135/136, 303-324.
James, A. M.; Laxman, R. K.; Fronczek, F. R.; Maverick, A. W. *Inorg. Chem.* 1998, 37, 3785-3791.
Kutal, C. *Coord. Chem. Rev.* 1990, 99, 213-252.
Lee, C.; Yang, W.; Parr, R. G.; *Phys. Rev. B* 1988, 37, 785-789.
Mankad, N. P.; Antholine, W. E.; Szilagyi, R. K.; Peters, J.C. *J. Am. Chem.. Soc.* 2009, 131, 3878-3880.
McMillin, D. R.; McNett, K. M. *Chem. Rev.* 1998, 98, 1201-1219.
Müller, P. *Crystallography Reviews*, 2009, 15, 57-83.
Müller, P.; Herbst-Irmer, R.; Spek, A. L.; Schneider, T. R.; Sawaya, M. R. *Crystal Structure Refinement: A Crystallographer's Guide to SHELXL*; Oxford University Press: New York, 2003.

(Continued)

*Primary Examiner* — David W Wu
*Assistant Examiner* — Vu A Nguyen
(74) *Attorney, Agent, or Firm* — Steptoe & Johnson LLP

(57) ABSTRACT

Monomeric metal complexes having desirable luminescence properties are provided. In one embodiment, a monomeric metal compound is represented by the formula $(ArN)M(L)_x$, where ArN is an arylamido ligand, and M may be any metal capable of exhibiting luminescent properties, for example, a $d^{10}$ metal. L may be a tertiary phosphine.

17 Claims, 13 Drawing Sheets

OTHER PUBLICATIONS

Noto, M.; Goto, Y.; Era, M. *Chem. Lett.* 2003, 32, 32-33.
Reiβ, P.; Fenske, D. *Z. Anorg. Allg. Chem.* 2000, 626, 1317-1331.
Robertson, N. *Chem. Sus. Chem.* 2008, 1, 977-979.
Sheldrick, G. M. (2008) *Acta Cryst.* A64, 112-122.
Sheldrick, G. M. *Cell_Now*; University of Göttingen, Göttingen, Germany.
Tomas, S. L.; Yagi, S.; Swager, T. M.; *J. Mater. Chem.* 2005, 15, 2829-2835.
V. A. Rassolov, J. A. Pople, M. A. Ratner, and T. L. Windus, "6-31G* basis set for atoms K through Zn," *J. Chem. Phys.*, 109 (1998) 1223-29.
V. A. Rassolov, M. A. Ratner, J. A. Pople, P. C. Redfern, and L. A. Curtiss, "6-31G* Basis Set for Third-Row Atoms," *J. Comp. Chem.*, 22 (2001) 976-84.
van Leeuwen et al., *Chem. Rev.* 2000, 100, 8.
Zolo, R. F.; Lipton, S.; Dori, Z. *Chem. Comm.* 1970, 1124-1125.

* cited by examiner

Select Bond lengths [A] and angles [°] for (Ph₃P)₂Cu(NPh₂) (1).

| | | | |
|---|---|---|---|
| Cu(1)-N(1) | 1.9602(15) | P(2)-Cu(1)-P(1) | 123.995(19) |
| Cu(1)-P(2) | 2.2436(5) | C(1B)-N(1)-C(7) | 130.6(10) |
| Cu(1)-P(1) | 2.2598(5) | C(1B)-N(1)-C(1A) | 15.7(10) |
| N(1)-C(1A) | 1.411(6) | C(7)-N(1)-C(1A) | 117.7(3) |
| N(1)-C(1B) | 1.36(3) | C(1A)-N(1)-Cu(1) | 123.5(3) |
| N(1)-C(7) | 1.395(2) | C(1B)-N(1)-Cu(1) | 111.2(10) |
| N(1)-Cu(1)-P(2) | 120.72(5) | C(7)-N(1)-Cu(1) | 118.14(12) |
| N(1)-Cu(1)-P(1) | 115.29(5) | | |

Select bond lengths [Å] and angles [°] for (Ph₃P)₂Cu(NTol₂) (2).

| | | | |
|---|---|---|---|
| Cu(1)-N(1) | 1.9363(15) | N(1)-Cu(1)-P(2) | 117.18(5) |
| Cu(1)-P(1) | 2.2215(6) | P(1)-Cu(1)-P(2) | 125.21(2) |
| Cu(1)-P(2) | 2.2362(6) | C(1)-N(1)-C(8) | 120.25(15) |
| N(1)-C(1) | 1.388(2) | C(1)-N(1)-Cu(1) | 120.18(12) |
| N(1)-C(8) | 1.389(2) | C(8)-N(1)-Cu(1) | 119.56(12) |
| N(1)-Cu(1)-P(1) | 117.60(5) | | |

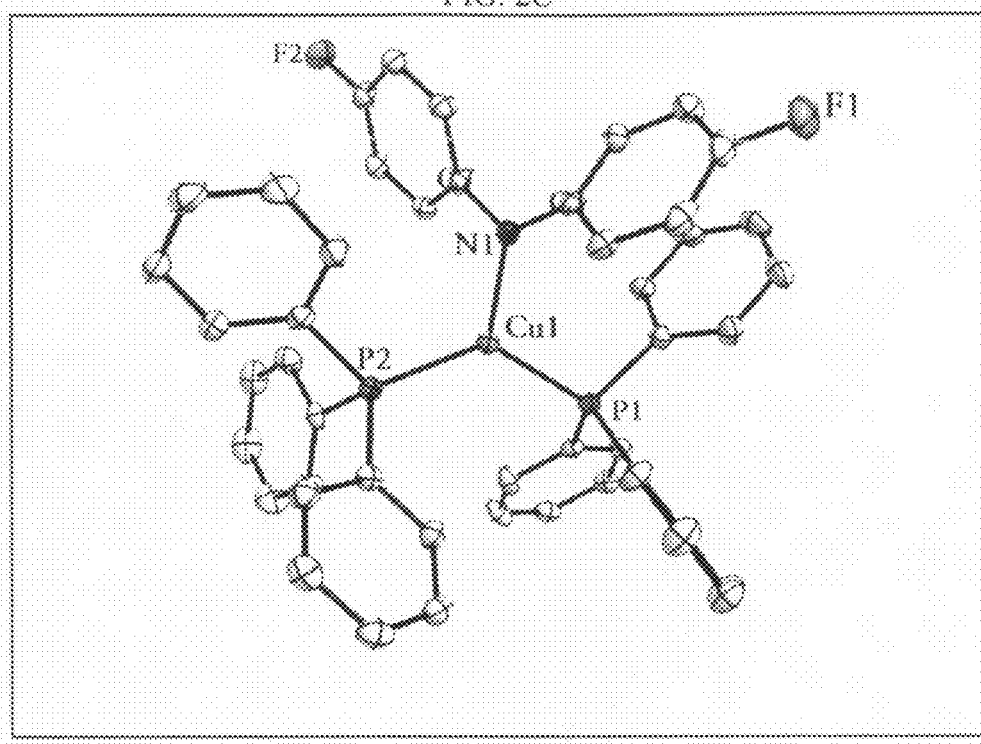
Select bond lengths [Å] and angles [°] for (Ph₃P)₂Cu(N(p-FPh)₂) (3).
| | | | |
|---|---|---|---|
| N(1)-C(7) | 1.381(2) | C(7)-N(1)-Cu(1) | 121.50(13) |
| N(1)-C(1) | 1.383(2) | C(1)-N(1)-Cu(1) | 119.02(13) |
| N(1)-Cu(1) | 1.9547(18) | N(1)-Cu(1)-P(2) | 118.88(5) |
| Cu(1)-P(2) | 2.2200(6) | N(1)-Cu(1)-P(1) | 111.27(5) |
| Cu(1)-P(1) | 2.2414(6) | P(2)-Cu(1)-P(1) | 129.82(2) |
| C(7)-N(1)-C(1) | 119.43(17) | | |

Select bond lengths [Å] and angles [°] for (Ph₃P)₂Cu(cbz) (4).

| | | | |
|---|---|---|---|
| Cu(1)-N(1) | 1.9499(11) | N(1)-Cu(1)-P(1) | 115.34(3) |
| Cu(1)-P(2) | 2.2467(4) | P(2)-Cu(1)-P(1) | 123.616(14) |
| Cu(1)-P(1) | 2.2765(4) | C(7)-N(1)-C(1) | 104.97(10) |
| N(1)-C(7) | 1.3869(16) | C(7)-N(1)-Cu(1) | 126.98(9) |
| N(1)-C(1) | 1.3913(16) | C(1)-N(1)-Cu(1) | 124.93(9) |
| N(1)-Cu(1)-P(2) | 121.05(3) | | |

EMISSIVE METAL COMPLEXES

FEDERALLY SPONSORED RESEARCH OR DEVELOPMENT

This invention was made with government support under Grant Nos. CHE-0616782 and CHE-0802907, awarded by the National Science Foundation. The government has certain rights in this invention.

TECHNICAL FIELD

The present invention relates to emissive metal complexes and methods of making them.

BACKGROUND

Luminescent transition metal compounds have been widely studied for their use in biological imaging, photochemical catalysis, light-driven fuel production, and electroluminescent devices. Conventionally, noble metal emitters have been used, but the high cost of such emitters has led to the investigation of copper as a low cost, biologically relevant alternative. The most thoroughly studied copper emitters are monomers supported by modified polypyridine and phenanthroline ligands. However, these compounds suffer from low quantum efficiencies and short luminescence lifetimes.

Recently, copper (I) amidophosphine compounds have been identified as a new class of highly luminescent compounds. Mononuclear and binuclear copper (I) compounds featuring bidentate and tridentate arylamidophosphine ligands have been found to exhibit quantum efficiencies of as high as 70%. However, the syntheses of these compounds which includes catalytic aryl amination and the use of lithium reagents and/or strong phosphide nucleophiles, has limited the synthetic versatility of these compounds.

SUMMARY

In one aspect, a monomeric metal compound is represented by Formula I:

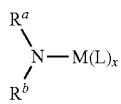

L can be $Z(R^c)_3$ or can have the formula:

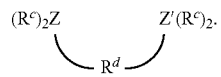

Z and Z', independently, can be N, P or As;

$R^c$ can be a group selected from an optionally substituted alkyl group, an optionally substituted alkenyl group, an optionally substituted alkynyl group, an optionally substituted aryl group, and an optionally substituted heteroaryl group.

$R^d$ can be a group selected from an optionally substituted alkylene group which can be optionally interrupted by O, S or $NR^b$, an optionally substituted arylene group, an optionally substituted heteroarylene group, an optionally substituted arylalkylene group, and an optionally substituted heteroarylalkylene group.

x can be 1 or 2.

M can be Cu, Ag, Au, Zn, Cd or Hg.

$R^a$ can be an optionally substituted aryl group.

$R^b$ can be an optionally substituted alkyl group, an optionally substituted alkenyl group, an optionally substituted alkynyl group, an optionally substituted aryl group, or an optionally substituted heteroaryl group.

Or, in some circumstances, $R^a$ and $R^b$ and N together can form an aryl group.

The compound can be represented by Formula II:

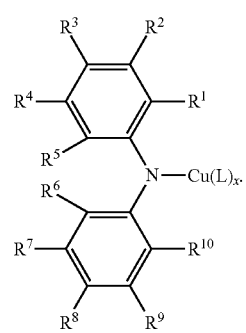

In Formula II, each of $R^1$ through $R^{10}$, independently, can be selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group.

Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group.

The compound can be represented by Formula III:

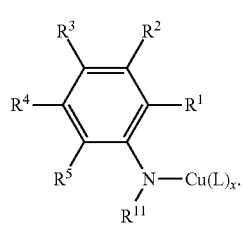

In Formula III, each of $R^1$ through $R^5$, independently, can be selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group.

$R^{11}$ can be selected from the group consisting of hydrogen, an acyl group, an optionally substituted alkyl group, an optionally substituted alkenyl group, an optionally substituted alkynyl group, an optionally substituted aryl group, and an optionally substituted heteroaryl group.

Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group.

The compound can be represented by Formula IV:

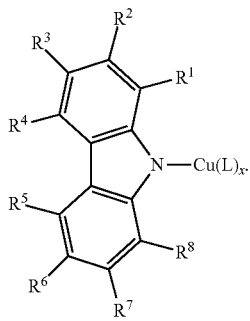

IV

In Formula IV, each of $R^1$ through $R^8$, independently, can be selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group.

Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group.

The compound can be represented by Formula V:

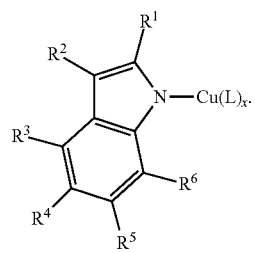

V

In Formula V, each of $R^1$ through $R^6$ independently, can be selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group.

Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group.

The compound can be represented by Formula VI:

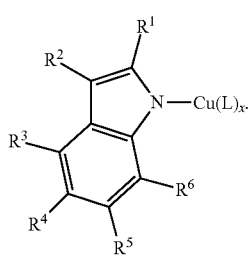

VI

In Formula VI, each of $R^1$ through $R^6$ independently, can be selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group.

Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group.

When L has the formula

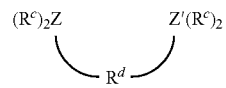

x can be 1 and Z and Z' can each independently be P. L can be a bisphosphinoalkane family ligand, a BISBI family ligand, a DPPF family ligand, a XANTphos family ligand, or a BINAP family ligand.

The compound can be $(Ph_3P)_2Cu(NPh_2)$, $(Ph_3P)_2Cu(NTol_2)$, $(Ph_3P)_2Cu(N(\rho\text{-}FPH)_2)$, or $(Ph_3P)_2Cu(cbz)$.

In another aspect, a luminescent device can include a compound represented by Formula I as described above. The device can further include an electric power source configured to electrically excite the compound.

In another aspect, a method of generating light includes exciting a compound represented by Formula I as described above. Exciting the compound can include photoexcitation or electrical excitation.

DESCRIPTION OF DRAWINGS

FIG. 2a-d are displacement ellipsoid representations of: (a) copper compound 1, $(Ph_3P)_2Cu(NPh_2)$; (b) copper compound 2, $(Ph_3P)_2Cu(NTol_2)$; (c) copper compound 3, $(Ph_3P)_2Cu(N(\rho\text{-}FPH)_2)$; and (d) copper compound 4, $(Ph_3P)_2Cu(cbz)$, with respective bond angles. Hydrogen atoms, solvent (benzene), and minor component of disorder omitted.

copper compound 2, (Ph$_3$P)$_2$Cu(NTol$_2$); (c) copper compound 3, (Ph$_3$P)$_2$Cu(N(ρ-FPH)$_2$); and (d) copper compound 4, (Ph$_3$P)$_2$Cu(cbz).

Figure 10:
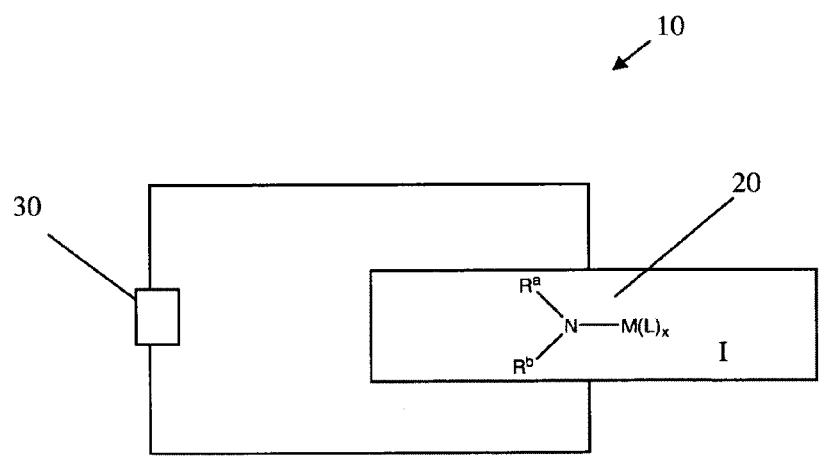

FIG. 10 is schematic diagram showing a device.

DETAILED DESCRIPTION

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl, trichloromethyl, trifluoromethyl and the like.

The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like.

The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like.

The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like.

The term "($C_1$-$C_{10}$)alkoxy" refers to an alkyl group attached through an oxygen atom. Examples of ($C_1$-$C_{10}$) alkoxy can be methoxy, ethoxy, propoxy, isopropoxy, butoxy, iso-butoxy, sec-butoxy, pentoxy, 3-pentoxy, or hexyloxy and the like.

The term "$C_3$-$C_{12}$ cycloalkyl" refers to a cyclic alkyl group, such as, for example, cyclopropyl, cyclobutyl, cyclopentyl, cyclohexyl, cycloheptyl, cyclooctyl and the like. Cycloalkyl groups include bicyclic groups such as decalinyl, bridged bicyclic groups such as norbornyl and bicyclo[2.2.2]octyl, tricyclic, bridged tricyclic such as adamantyl, and spiro-linked bicyclic or tricyclic groups.

The term "($C_6$-$C_{14}$)aryl" refers to a monocyclic, bicyclic, or tricyclic carbocyclic ring system having one or two aromatic rings including, but not limited to, phenyl, benzyl, naphthyl, tetrahydronaphthyl, indanyl, indenyl, anthracyl, and the like.

The term "aryl($C_1$-$C_{20}$)alkyl" or "arylalkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "($C_1$-$C_{14}$)heterocyclic group" refers to an optionally substituted mono- or bicyclic carbocyclic ring system containing one, two, three, or four heteroatoms (optionally in each ring) wherein the heteroatoms are oxygen, sulfur, and nitrogen.

The term "($C_4$-$C_{14}$)heteroaryl" refers to an optionally substituted mono- or bicyclic cyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

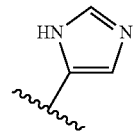

is understood to represent a mixture of the structures:

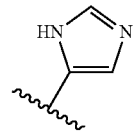

as well as

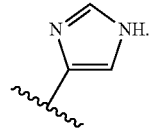

Mononuclear metal arylamido complexes, for example, copper (I) arylamidophosphine compounds have excellent emission and luminescence properties. The complexes that can be quickly assembled from common, commercially available reagents such as diphenylamine and triphenylphosphine. The compounds have structures that are easily manipulable. Ease of manipulation is one important benefit of these compounds because manipulation of the compound structure enables easy modification of the properties of the compound and easy tuning of the color and luminescence properties of the compound.

In one embodiment, a monomeric metal compound has Formula I:

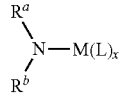

wherein:
L is Z(R$^c$)$_3$;
Z is N, P or As;
R$^c$ is a group selected from an alkyl group, alkenyl group, alkynyl group, aryl group, and heteroaryl group;
x is 1 or 2;
M is Cu, Ag, Au, Zn, Cd or Hg; and
R$^a$ is an aryl group;
R$^b$ is an alkyl group, alkenyl group, alkynyl group, aryl group, or heteroalkyl group; or
R$^a$ and R$^b$ and N together form an aryl group.

As shown in Formula I, M is bonded to an arylamido ligand and one or more additional ligands (L). M may be any metal capable of producing emission characteristics. In one embodiment, for example, M is a $d^{10}$ metal. Nonlimiting examples of suitable metals for M include Cu, Ag, Zn, Cd and Hg. In one embodiment, for example, M is Cu, and these Cu compounds exhibit unusually long lifetimes (about 16 to about 150 µS), extremely high quantum efficiency (Φ ranging from 0.16 to about 0.70), and variable emission maxima ranging from about 500 nm to about 550 nm in benzene at 298 K.

In some cases, additional ligand L can be a bidentate, chelating ligand. The bidentate chelating ligand can have the following formula:

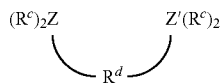

where Z and Z', independently, can be N, P or As. Each $R^c$, independently, can be selected from the group consisting of hydrogen, an optionally substituted alkyl group, an optionally substituted alkenyl group, an optionally substituted alkynyl group, an optionally substituted aryl group, and an optionally substituted heteroaryl group, and $R^d$ is a bivalent linking group. Specifically, $R^d$ can be an optionally substituted alkylene group which can be optionally interrupted by O, S or $NR^b$, an optionally substituted arylene group, an optionally substituted heteroarylene group, an optionally substituted arylalkylene group, or an optionally substituted heteroarylalkylene group.

In this context, "heteroarylene" includes sandwich groups, for example metallocene groups, such that Z is bound to an atom of a first coordinating arene and Z' is bound to an atom of a second coordinating arene.

In this context, "arylalkylene" refers to linking groups including both an aryl moiety and an alkyl moiety. Z and Z', independently may be bound to an aryl moiety or an alkyl moiety. Similarly, "heteroarylalkylene" refers to linking groups including both a heteroaryl moiety and an alkyl moiety.

In some circumstances, Z and Z' are both P, such that L is a bidentate, chelating phosphine ligand. Certain families of bidentate chelating phosphine ligands may be suitable. One such family is the bisphosphinoalkane ligands, where $R^d$ is an optionally substituted alkylene group.

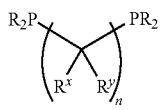

bisphosphinoalkanes

R: alkyl or aryl (either may be substituted)
$R^x$, $R^y$: H, halo, OH, CN, $NO_2$, $NR_2$, OR, C(O)R, alkyl
n: 1-4

In this family, $R^d$ can be, for example, methanediyl, 1,2-ethanediyl, or 1,3-propanediyl. Exemplary bisphosphinoalkane ligands include 1,1-bis(diphenylphosphino)methane (dppm), 1,2-bis(diphenylphosphino)ethane (dppe), 1,3-bis(diphenylphosphino)propane (dppp), and 1,2-bis(ditertbutylphosphino)ethane (dtbpe).

Another family is the BISBI family of bidentate chelating phosphine ligands. In this family, $R^d$ is an optionally substituted arylalkylene group, e.g., 2,2'-bis(methylene)-1,1'-biphenyl.

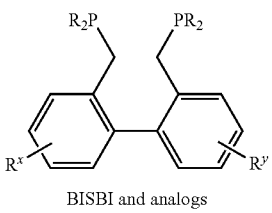

BISBI and analogs

R: alkyl or aryl (either may be substituted)
$R^x$, $R^y$: H, halo, OH, CN, $NO_2$, $NR_2$, OR, C(O)R, alkyl BISBI refers to the prototypical member of this family, 2,2'-bis(diphenylphosphinomethyl)-1,1'-biphenyl. Substituted analogs of BISBI are included in this family as well.

A further family is the DPPF family of bidentate chelating phosphine ligands. In this family, $R^d$ is a metallocene moiety where $E^1$ and $E^2$ are bound separately to the two cyclopentadienyl rings.

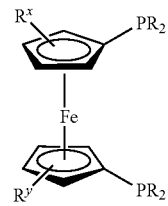

DPPF and analogs

R: alkyl or aryl (either may be substituted)
$R^x$, $R^y$: H, halo, OH, CN, $NO_2$, $NR_2$, OR, C(O)R, alkyl The prototypical member of this family is the DPPF ligand, 1,1'-bis(diphenylphosphino)ferrocene, where $R^d$ is 1,1'-bis(ferrocene)diyl. Substituted analogs of DPPF, including both substitutions of the cyclopentadienyl rings and of the metal atom, are included in this family.

Still another family is the XANTphos family of bidentate chelating phosphine ligands. XANTphos refers to the prototypical member of this family, 4,5-bis(diphenylphosphino)-9,9-dimethylxanthene. In this family, $R^d$ is an optionally substituted heteroalkylene group. In general, a member of the XANTphos family has the following structure:

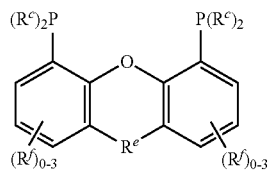

where $R^e$ can be a bond, $NR^g$, $PR^g$, S, di(alkyl)Si, an optionally substituted alkylene group, or $R^e$ can be absent. In some cases, $R^e$ and one $R^f$, together with the atoms to which the are attached, form a 5 to 7 membered ring. Each $R^f$, independently, can be hydrogen, alkyl, hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, or an optionally substituted heteroaryl group. $R^g$ can be hydrogen, an optionally substituted alkyl group, an optionally substituted alkenyl group, an optionally substituted alkynyl group, an optionally substituted aryl group, and an optionally substituted heteroaryl group.

Exemplary member of the XANTphos family include its prototypical member, XANTphos; DPEphos, homoxantphos, phosxantphos, sixantphos, thiaxantphos, isopropxantphos, benzylnixantphos, nixantphos, benzoxantphos, dbfphos, and t-Bu-xantphos (see, for example, van Leeuwen et al., *Chem. Rev.* 2000, 100, 8, especially at 2746, which is incorporated by reference in its entirety).

Yet another family of bidentate chelating phosphine ligands is the BINAP family. BINAP refers to the prototypical member of the family, 2,2'-bis(diphenylphosphino)-1,1'-binaphthyl. In the BINAP family, $R^d$ is an optionally substituted arylene group.

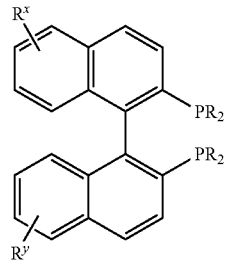

BINAP and analogs
(stereochemistry not shown)

R: alkyl or aryl (either may be substituted)
$R^x$, $R^y$: H, halo, OH, CN, $NO_2$, $NR_2$, OR, C(O)R, alkyl Substituted analogs of BINAP are included in the family. BINAP and other members of the BINAP family are chiral, and either the R or S enantiomer, or a mixture of the two, can be used.

In one embodiment of Formula I, $R^a$ can be an aryl group and $R^b$ can be a group selected from an alkyl group, alkenyl group, alkynyl group, aryl group, and heteroalkyl group; M can be Cu. In the case of a monodentate ligand, Z can be P, and x can be 2. In the case of a bidentate ligand, Z and Z' can each independently be P, and x can be 1. In some circumstances, both $R^a$ and $R^b$, independently, can be an aryl group. According to this embodiment, the emissive metal compounds are represented by Formulas II-III:

Formula II:

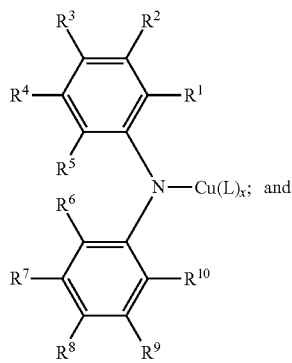

Formula III:

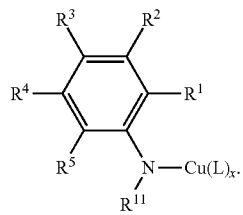

In another embodiment of Formula I, $R^a$ and $R^b$ and N together form an aryl group, M can be Cu. In the case of a monodentate ligand, Z can be P, and x can be 2. In the case of a bidentate ligand, Z and Z' can each independently be P, and x can be 1. According to his embodiment, the emissive metal compounds are represented by Formulas IV-VI:

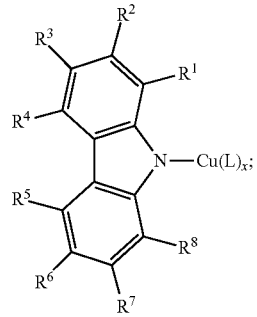

IV

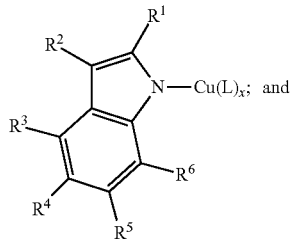

V

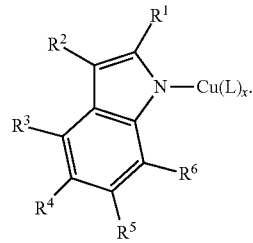

VI

In Formulas II-VI, $R^1$ through $R^{10}$ can each independently be hydrogen or any other substituent. Substituents for substituting aryl rings are well known, and any such known substituents may be used for $R^1$ through $R^{10}$. Nonlimiting examples of suitable substituents for $R^1$ through $R^{10}$ include hydrogen, halogens, hydroxyl groups, cyano groups, alkoxy groups, acyl groups, substituted or unsubstituted alkyl groups, substituted or unsubstituted alkenyl groups, substituted or unsubstituted alkynyl groups, substituted or unsubstituted aryl groups, substituted or unsubstituted heteroaryl groups, and the like. In one embodiment, at least one of $R^1$ through $R^{10}$ is selected from a methyl group or a trihalosubstituted methyl group, such as a trifluoro methyl group.

The emission properties of the compound can be fine tuned by selecting the substitutents on the aryl ring(s) of $R^a$ and/or $R^b$. For example, emission efficiency may be tuned by including an electron donating or electron withdrawing group on the arene backbone of the arylamido ligand. Nonlimiting examples of such groups include methyl groups and trifluoromethyl groups.

Each $R^c$ group can, in some circumstances, each independently be any hydrocarbon substituent. Nonlimiting examples of suitable hydrocarbon substituents for $R^c$ include alkyl groups, alkenyl groups, alkynyl groups, aryl groups, and the like. In one embodiment, for example, L can be a hydrocarbon phosphine P(R$^c$)$_3$, such as, for example, trimethylphosphine, triethylphosphine, tripropylphosphine, tri-t-butylphosphine, triphenylphosphine, etc. In another embodiment, L can be any commerically available monodentate or bidentate phosphine ligand including those in which all three substituents are the same, those in which two substituents are the same and one is different, and those in which all three substituents are different. In addition, any aryl rings or alkyl groups of R$^c$ can be substituted at any position with any suitable substituent. Generally, any substituent suitable for R$^1$ through R$^{10}$ groups can also be suitable for substituents on R$^c$.

Compounds can be prepared by treating a suspension of a metal salt in a suitable solvent, e.g., benzene or toluene, a sufficient quantity of the desired ligand(s) L to provide two equivalents of donor atoms (for example, two equivalents of a monodentate ligand L, or one equivalent of a bidentate chelating ligand L). Ligand L can be a tertiary phosphine, such as triphenylphoshine. The following step is a salt metathesis with the corresponding lithium precursor of the arylamido ligand. To prepare compounds of copper, CuBr.SMe$_2$ can be the metal salt. In one embodiment, to form a compound of Formula IV-VI, the rings of the lithium precursor may be fused by any suitable means, for example, via a Goldberg coupling.

To prepare compounds of other metals, for example Ag and Zn, the CuBr.SMe$_2$ solution can be replaced with a suitable solution for preparing compounds of the desired metal. For example, to prepare an Ag compound, AgOTf and diethyl ether can be used. As another example, a Zn compound can be prepared using ZnCl$_2$ and THF (tetrahydrofuran). More specific examples of the synthesis of various exemplary compounds of the invention are described in the below Examples.

EXAMPLES

In the Examples, manipulations were carried out under a dinitrogen atmosphere using standard glovebox techniques. All solvents were deoxygenated and dried by sparging with Ar followed by passage through an activated alumina column from S. G. Water (Nashua, N.H.) Solvents were tested with a standard purple solution of benzophenone ketyl in THF to confirm effective oxygen and moisture removal. Methylcyclohexane (MeCy) was of spectroscopic grade. Deuterated solvents were purchased from Cambridge Isotope Laboratories, Inc. and were degassed and stored over 3 Å molecular sieves prior to use. Bis-(4-fluorophenyl)amine and mesityl copper(I) were prepared according to literature procedures. See, for example, Fan, L.; Yang, L.; Guo, C.; Foxman, B. M.; Ozerov, O. V. *Organometallics* 2004, 23, 4778-4787 and Eriksson, H.; Hkansson, M. *Organometallics*, 1997, 16, 4243-4244, each of which is incorporated in its entirety. Lithium amides were prepared from the corresponding aryl amines by treatment with a hexane solution of n-butyllithium at −78° C. The stoichiometry of coordinated solvent molecules in the lithium reagents was determined from $^1$H NMR spectroscopy. Celite (Celite® 545) was dried at 300° C. under vacuum for 48 hours. Glass microfiber filters were dried prior to use by heating at 350° C. for 48 hours. All other starting reagents and materials were obtained from commercial vendors and used without further purification. Elemental analyses were performed by Midwest Microlabs (Indianapolis, Ind.). NMR spectra were recorded at ambient temperature on Bruker Avance 400 MHz spectrophotometers. $^1$H and $^{13}$C spectra are referenced to residual solvent. $^{31}$P spectra are reported relative to an external standard of 85% H$_3$PO$_4$ (δ=0 ppm). $^{19}$F spectra are reported relative to an external standard of C$_6$F$_6$ (δ=−164.9 ppm). UV-Vis absorption measurements were recorded on a Varian Cary 50 UV-Vis spectrophotometer using 1 cm path length quartz cuvettes equipped with an air-tight silicone-lined screw cap.

Figure 6:
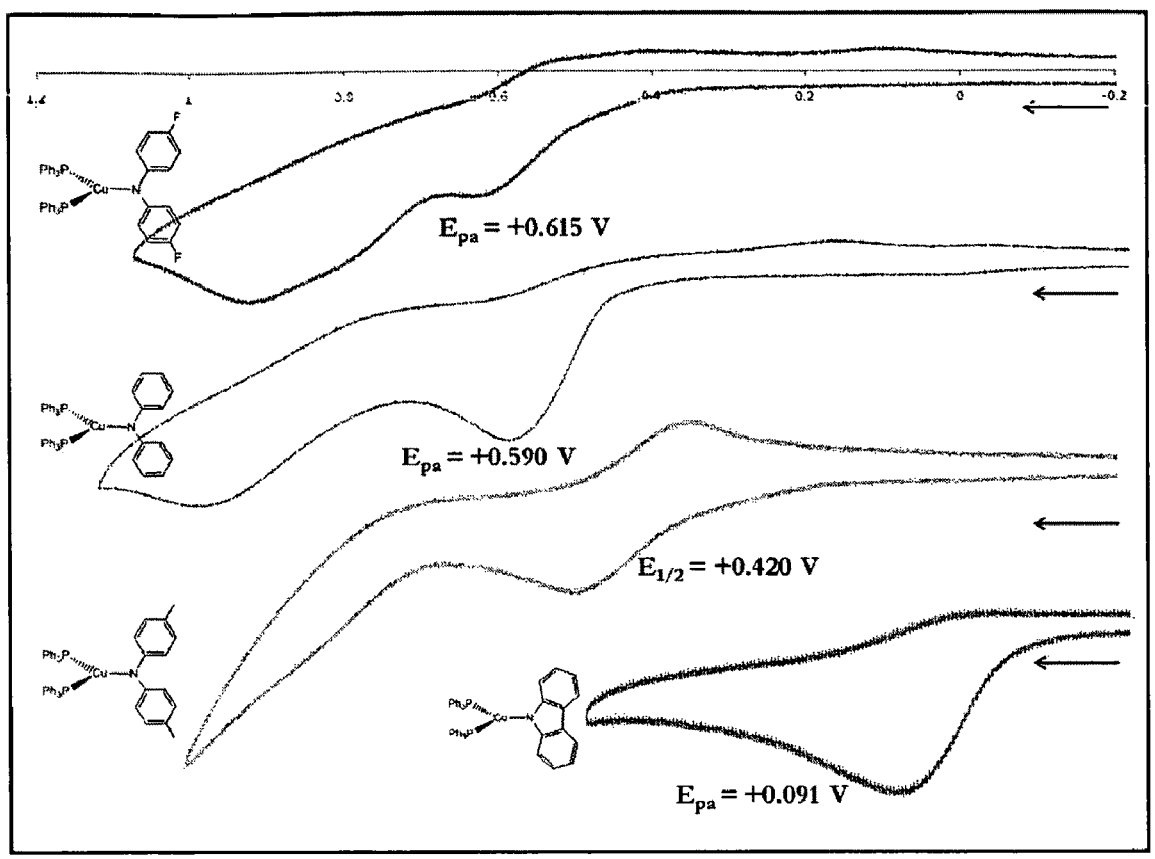
FIG. 6 is cyclic voltammograms of copper compounds 1-4 in 0.3 M $TBAPF_6$ electrolyte solution in THF.
Figure 7:
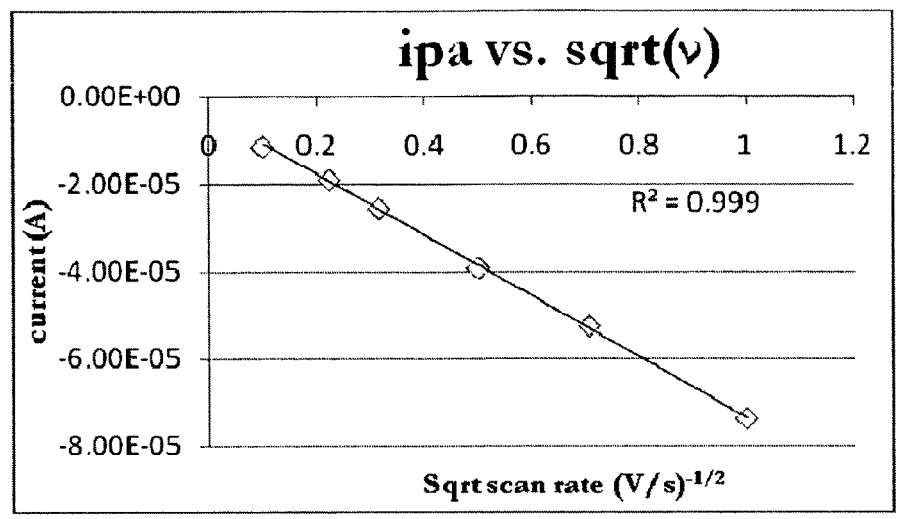
FIG. 7 is a graph showing oxidative peak current as a function of $v^{1/2}$ for copper compound 2, $(Ph_3P)_2Cu(NTol_2)$.
Figure 8A:
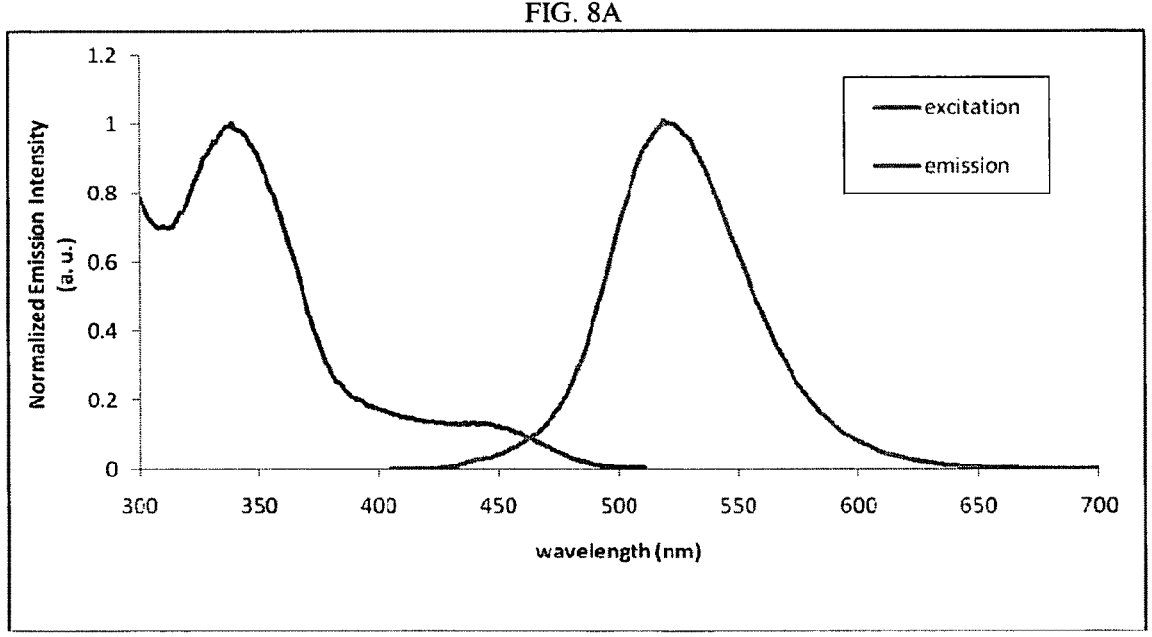
FIG. 8a-d are excitation and emission spectra of: (a) copper compound 1, $(Ph_3P)_2Cu(NPh_2)$; (b) copper compound 2, $(Ph_3P)_2Cu(NTol_2)$; (c) copper compound 3, $(Ph_3P)_2Cu(N(\rho\text{-}FPH)_2)$; and (d) copper compound 4, $(Ph_3P)_2Cu(cbz)$.
Figure 8B:
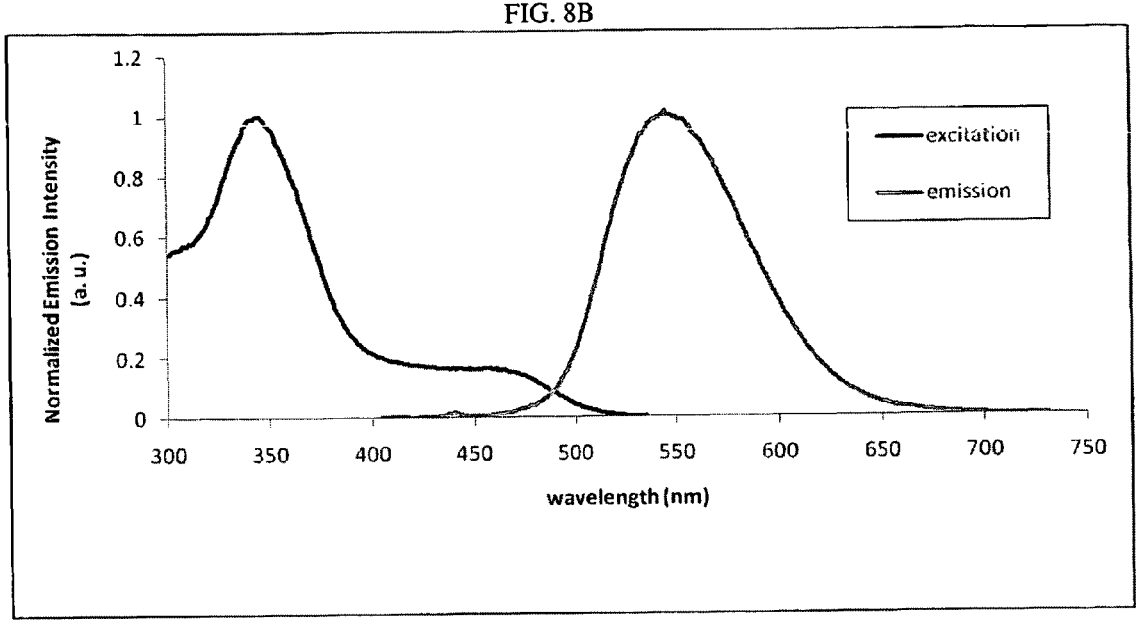
Figure 8C:
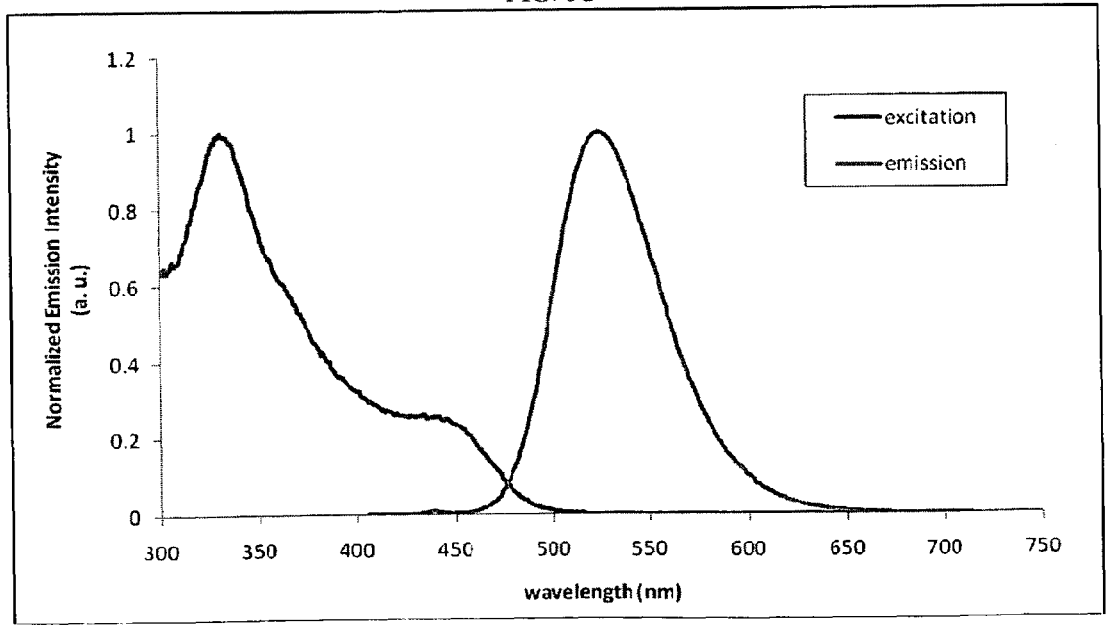
Figure 8D:
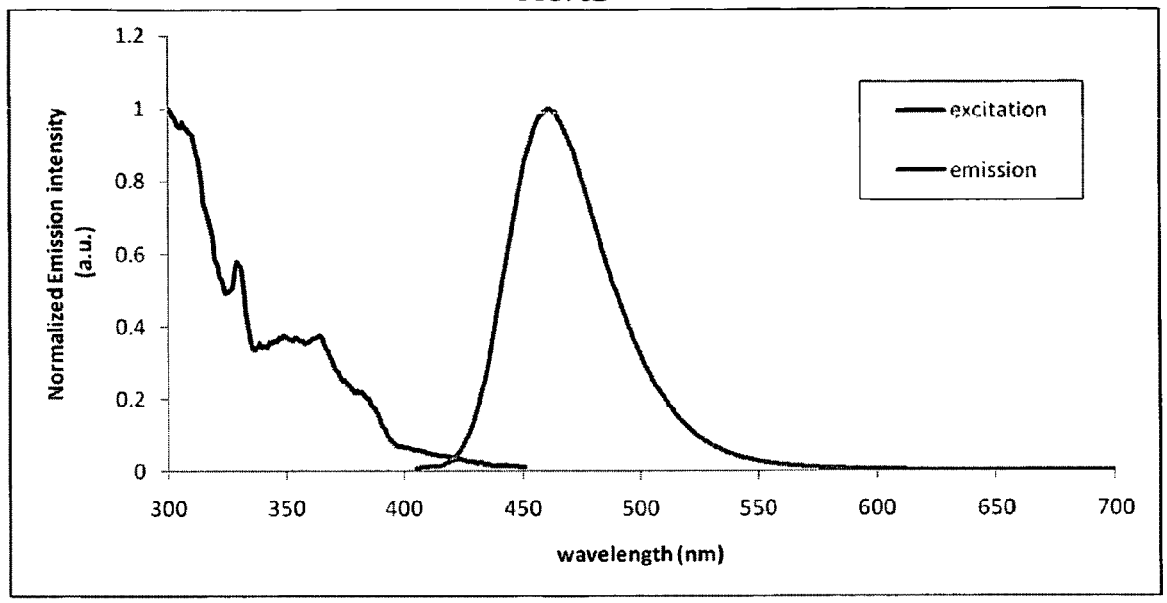
Figure 9A:
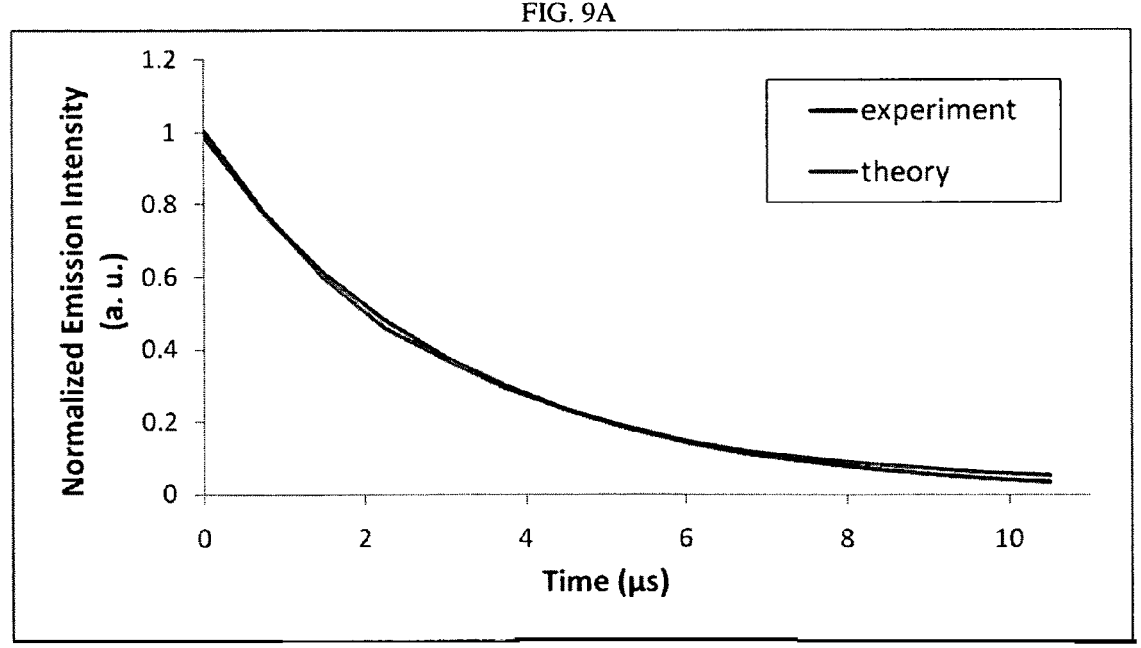
FIG. 9a-d are luminescence decay traces with monoexponential fit of: (a) copper compound 1, $(Ph_3P)_2Cu(NPh_2)$; (b)
Figure 9B:
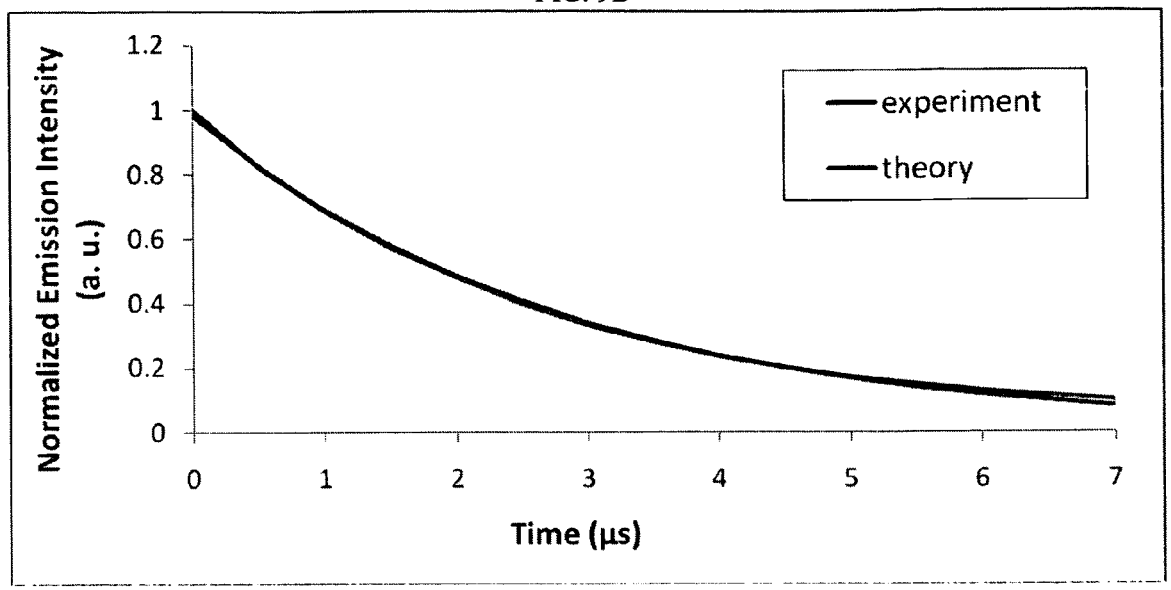
Figure 9C:
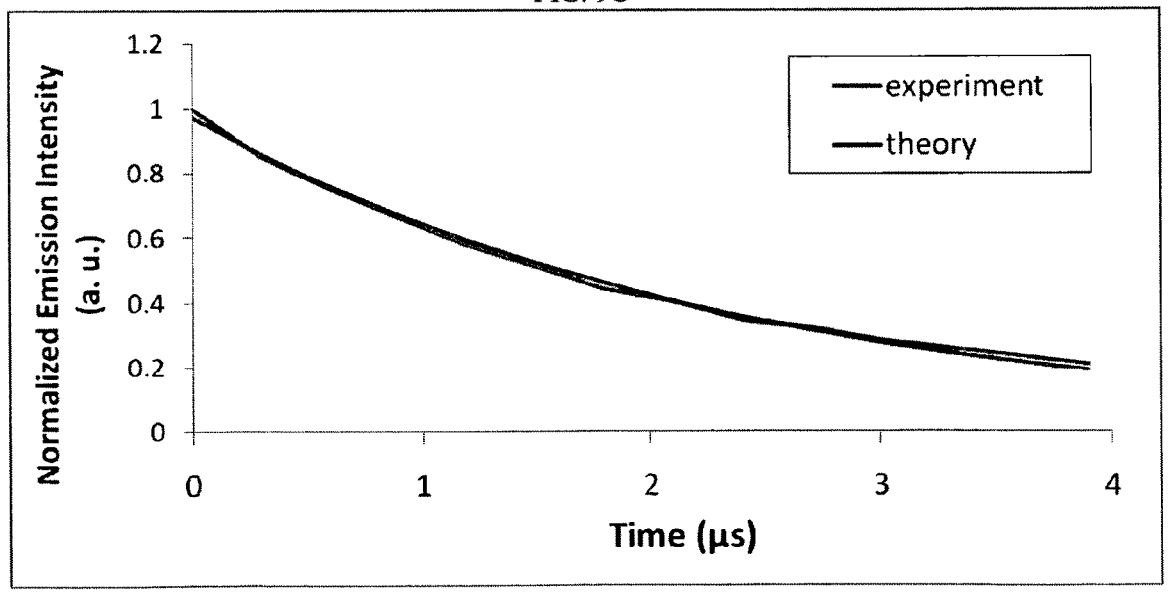
Figure 9D:
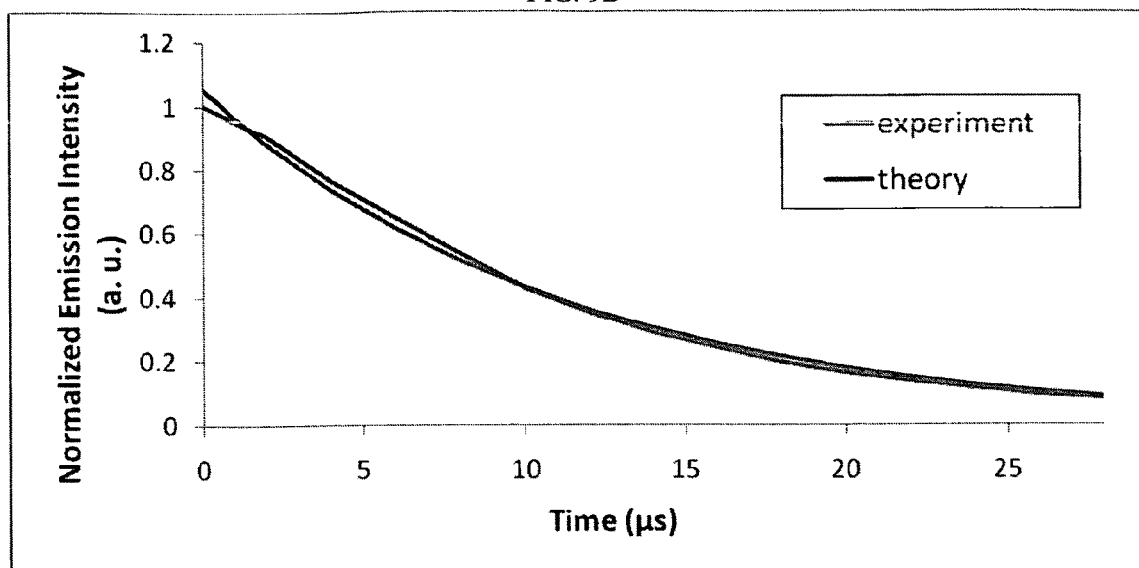

Electrochemical measurements were carried out in a glovebox under a dinitrogen atmosphere in a single-compartment cell using a BAS model 100/W electrochemical analyzer. A freshly polished glassy carbon electrode and a coiled platinum wire were used as the working and auxiliary electrodes, respectively. The reference electrode was Ag/AgNO$_3$ solution in THF. Samples were prepared by dissolving a small quantity (ca. 3 mg) of analyte in approximately 3 mL of a 0.3 M [(Bu)$_4$N][PF$_6$] electrolyte solution in THF. In FIG. 6, the cyclic voltammagrams of the samples are shown. FIG. 7 shows oxidative peak current $i_{pa}$ as a function of $v^{1/2}$ for compound 2, (Ph$_3$P)$_2$Cu(NTol$_2$). The reference electrode was calibrated before and after measurements using an external ferrocene standard.

Figure 1:
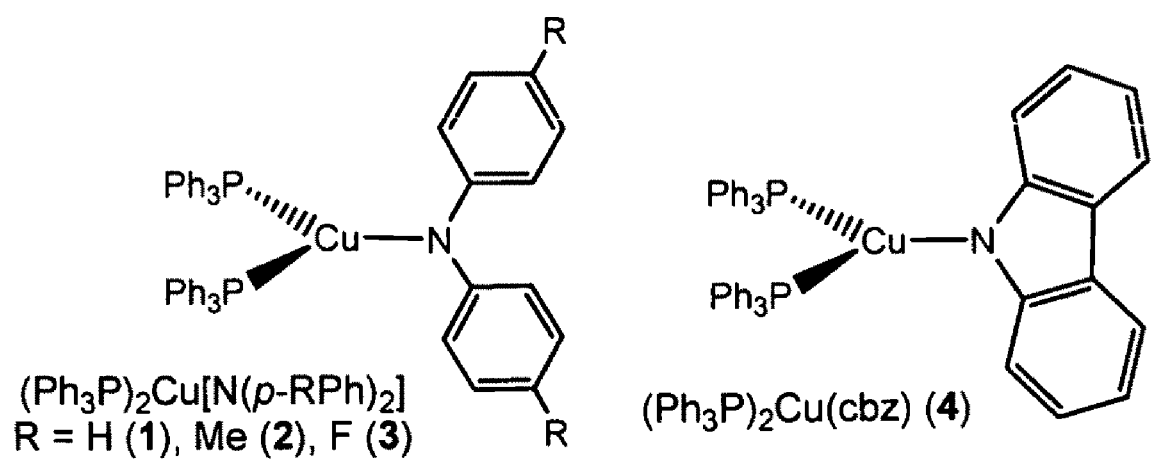
FIG. 1 includes schematic representations of copper compound 1, $(Ph_3P)_2Cu(NPh_2)$; copper compound 2, $(Ph_3P)_2Cu(NTol_2)$; copper compound 3, $(Ph_3P)_2Cu(N(\rho\text{-}FPH)_2)$ (left); and copper compound 4, $(Ph_3P)_2Cu(cbz)$ (right).
Figure 2A:
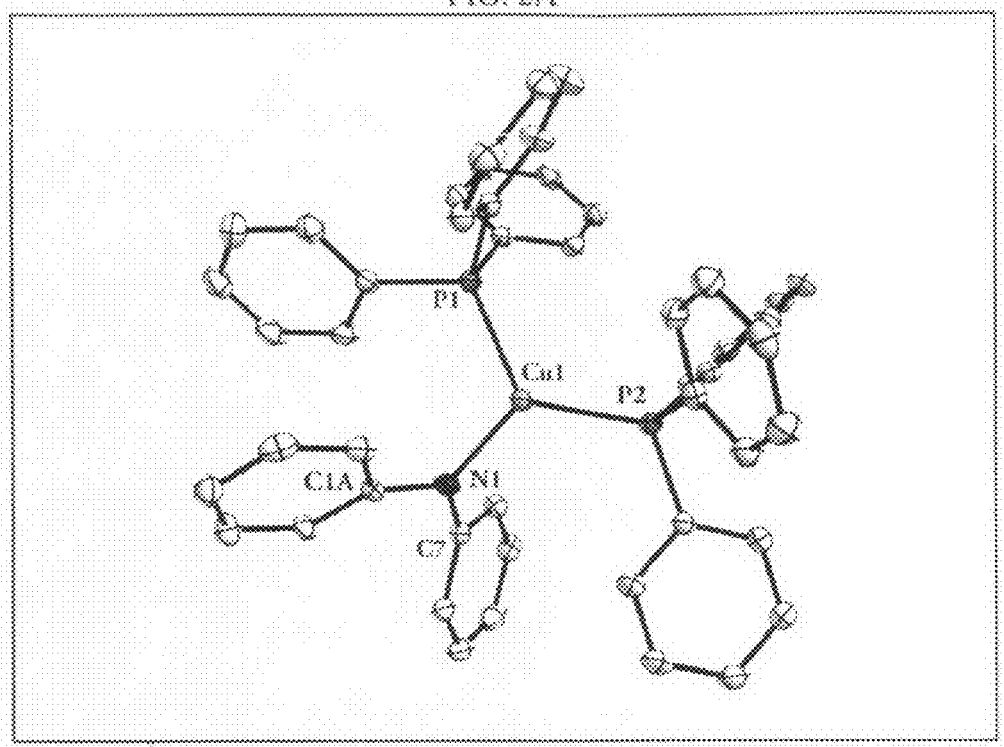
Figure 2B:
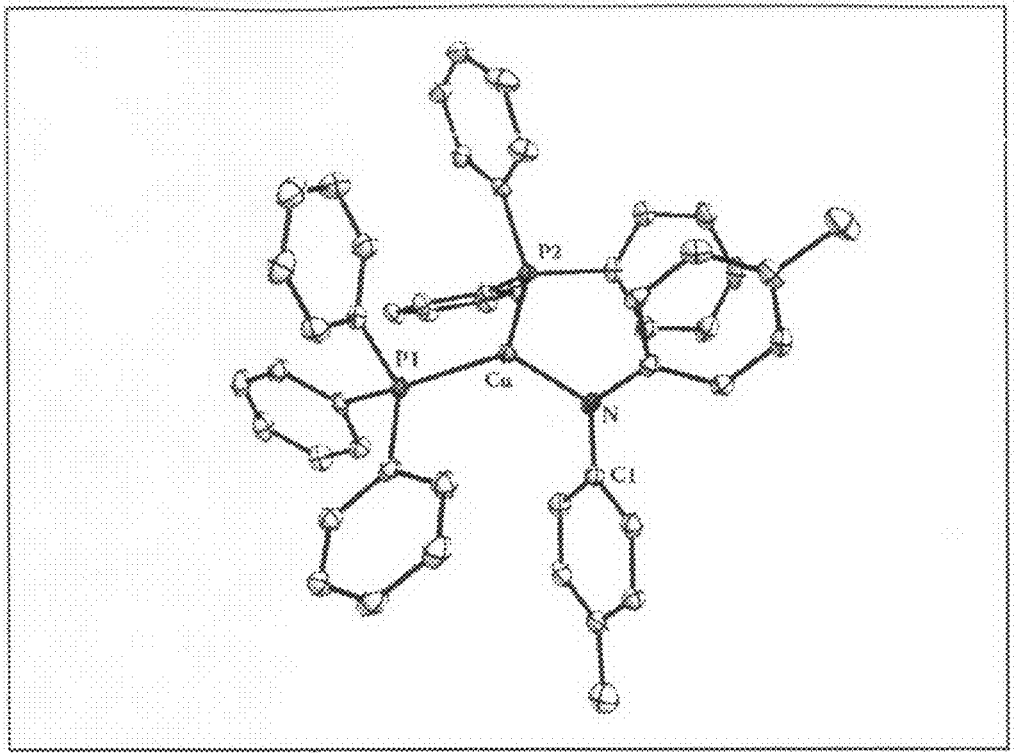
Figure 2D:
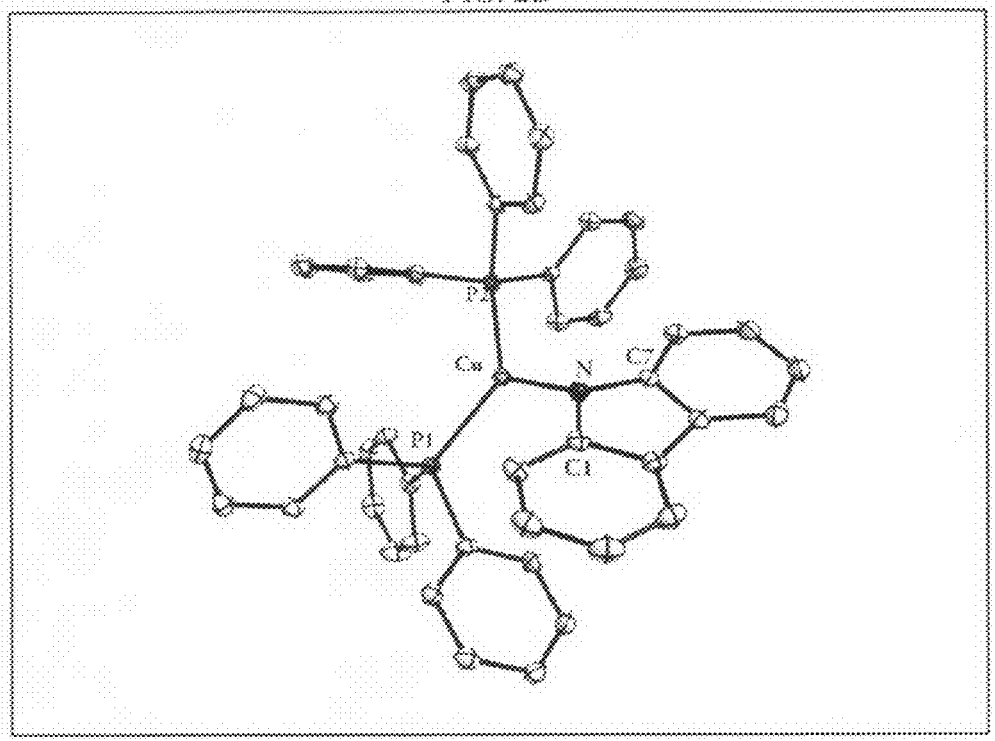

In FIG. 1, the copper compounds of Examples 1-4, respectively, are illustrated. The compounds were prepared by treating a suspension of CuBr.SMe$_2$ in benzene with two equivalents of triphenylphosphine followed by salt metathesis with the corresponding lithium amide. 1-3 were obtained as bright yellow-green luminescent solids while 4 was obtained as a pale yellow solid whose luminescence is only visible upon ultraviolet irradiation.

Analytically pure material of 1-4 was obtained in good to excellent yield (64-91%) following filtration to remove lithium bromide and recrystallization from a mixture of n-pentane and benzene. Alternatively, 1 was prepared in substantially lower yield (19%) by treating a benzene solution of mesitylcopper(I) with triphenylphosphine and diphenylamine, eliminating the use of lithium reagents entirely. In all cases, crystals suitable for single crystal X-ray diffraction were obtained by layering a benzene solution of 1-4 with pentane.

Example 1

Synthesis of (Ph$_3$P)$_2$Cu(NPh$_2$) (1)

Method A. A solution of triphenylphosphine (255 mg, 0.97 mmol, 2 eq.) in 3 mL benzene was added to a stirring suspension of CuBr.SMe$_2$ (100 mg, 0.49 mmol, 1 eq.) in 3 mL benzene causing the suspended solids to dissolve. Li(NPh$_2$).1.33 Et$_2$O (133 mg, 0.49 mmol, 1 eq.) was added dropwise as a suspension in 3 mL benzene to the stirring copper-phosphine mixture causing the immediate production of a bright green luminescence. The solution was stirred at ambient temperature for 5 h then concentrated in vacuo to a volume of 2 mL. The concentrated solution was passed through a glass microfiber filter packed with Celite. The filter was extracted with benzene until the total volume of the filtered solution was 5 mL. The solution was carefully layered with 15 mL n-pentane and allowed to stand undisturbed for 3 days after which large green-yellow crystalline blocks and needles had grown. The solution was cooled to −30° C. for 2 hr then filtered. The solids were rinsed once with n-pentane and briefly dried in vacuo. Yield: 312 mg (85%). $^1$H NMR (C$_6$D$_6$, 400 MHz): δ 7.50 (d, 4H, NAr—H), 7.35 (t, 12H, P(C$_6$H$_5$)$_3$), 7.13 (t, 4H, NAr—H), 7.00-6.88 (m, 18H, P(C$_6$H$_5$)$_3$), 6.70 (t, 2H, NAr—H). $^{31}$P{$^1$H} NMR(C$_6$D$_6$, 162 MHz): δ−2.01 (br). $^{13}$C{$^1$H} NMR(C$_6$D$_6$, 100 MHz): δ 134.20 (d, J$_{PC}$=15.4 Hz), 129.80, 129.41, 128.91 (d, J$_{PC}$=8.9 Hz), 120.89, 116.42. Anal. calcd. for C$_{50}$H$_{44}$CuNP$_2$C, 76.56; H, 5.65; N, 1.79; Found: C, 76.23; H, 5.65; N, 1.89.

Method B. A solution of triphenylphosphine (72 mg, 0.27 mmol, 2 eq.) in 3 mL benzene was added to a stirring solution of mesityl copper (25 mg, 0.14 mmol, 1 eq.) in 3 mL benzene causing the yellow solution to lighten slightly. After stiffing for ca. 5 minutes, diphenylamine (23 mg, 0.14 mmol, 1 eq.) in 3 mL benzene was added to the stirring copper-phosphine mixture. After stirring for 3 days at room temperature, a bright green luminescent solution had developed. The solvent was concentrated in vacuo to a volume of 2 mL, filtered through a glass microfiber filter packed with Celite. 10 mL n-pentane was added and the solution cooled to −30° C. overnight, affording a bright green microcrystalline solid. The solid was filtered, rinsed with n-pentane, and dried briefly in vacuo. Yield: 22 mg (19%). Spectroscopic data were identical to that of the material obtained by method A.

Example 2

Synthesis of $(Ph_3P)_2Cu(NTol_2)$ (2)

A solution of triphenylphosphine (255 mg, 0.97 mmol, 2 eq.) in 5 mL benzene was added to a stirring suspension of $CuBr.SMe_2$ (100 mg, 0.49 mmol, 1 eq.) in 10 mL benzene causing the suspended solids to dissolve. $Li(NTol_2).2 Et_2O$ (171 mg, 0.49 mmol, 1 eq.) was added dropwise as a suspension in 3 mL benzene to the stirring copper-phosphine mixture causing the production of an orange solution. The solution was stirred at ambient temperature overnight then passed twice through a glass microfiber filter packed with Celite. The filtered solution was lyophilized then dissolved in 65 mL of a 1.6:1 mixture of n-pentane and benzene. The solution was filtered again and cooled to −30° C. overnight giving a bright yellow solid. The solids were rinsed once with n-pentane and dried briefly in vacuo. Yield: 258 mg (68%). Crystals satisfactory for X-ray diffraction analysis were obtained by layering a concentrated solution of 2 in benzene with pentane, giving translucent yellow blocks overnight. $^1H$ NMR($C_6D_6$, 400 MHz): δ 7.44 (d, 4H, NAr—H), 7.35 (t, 12H, $P(C_6H_5)_3$), 6.90-7.01 (m, 22H, NAr—H and $P(C_6H_5)_3$), 2.23 (s, 6H, Ar—$CH_3$). $^{31}P\{^1H\}$ NMR($C_6D_6$, 162 MHz): δ−2.01 (br). $^{13}C\{^1H\}$ NMR($C_6D_6$, 100 MHz): δ 134.25 (d, $J_{PC}$=16.1 Hz), 130.02, 129.65, 128.87 (d, $J_{PC}$=8.7 Hz). Anal. calcd. for $C_{58}H_{40}CuNP_2C$, 76.22; H, 5.33; N, 1.85; Found: C, 75.97; H, 5.40; N, 1.87.

Figure 4:
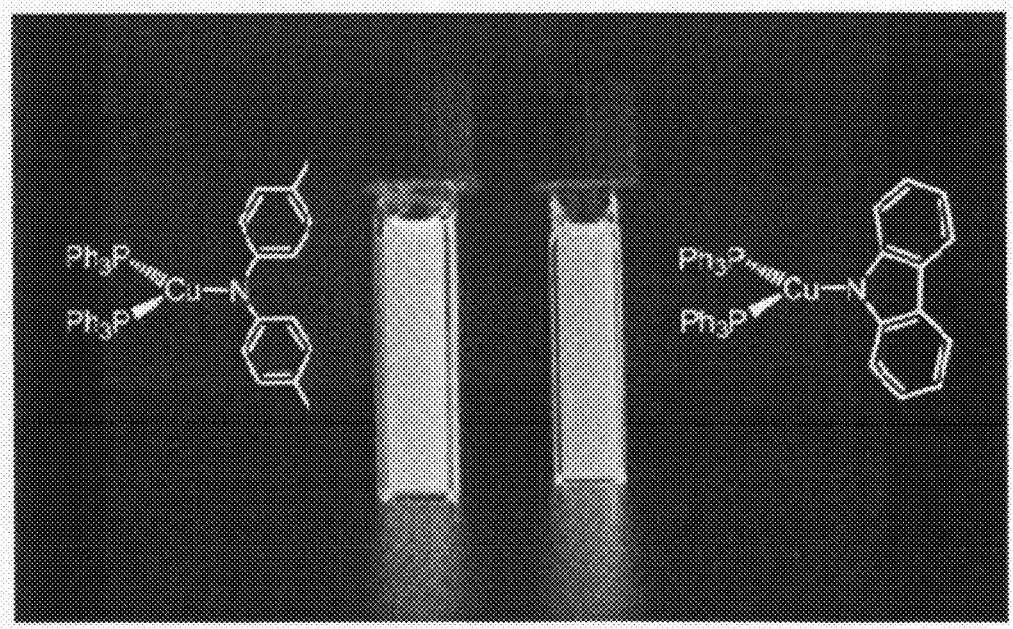
FIG. 4 is an image of photoluminescing copper compound 2 (left) and copper compound 4 (right).

FIG. 4 shows luminescence arising from a solution of copper compounds 2 (left) and 4 (right) under UV illumination. Compounds 1-4 had emission maxima that spanned 85 nm in the visible spectrum from 461 nm (blue) to 546 nm (green-yellow). Photoluminescence quantum yields ranged from 0.13 to 0.23 while radiative lifetimes ranged from 2.5 μs to 11.7 μs in methylcyclohexane solution at room temperature.

Example 3

Synthesis of $(Ph_3P)_2Cu(N(\rho\text{-FPH})_2)$ (3)

A solution of triphenylphosphine (255 mg, 0.97 mmol, 2 eq.) in 3 mL benzene was added to a stirring suspension of $CuBr.SMe_2$ (100 mg, 0.49 mmol, 1 eq.) in 3 mL benzene, causing the suspended solids to dissolve. A solution of Li(N(ρ-FPH)$_2$).0.66 $Et_2O$ in 3 mL benzene was added dropwise to the stirring copper-phosphine mixture causing the immediate production of a bright green luminescent solution. The solution was stirred at ambient temperature overnight then concentrated to ca. 2 mL in vacuo. The concentrated solution was filtered through a glass microfiber filter with Celite. The filter was extracted with benzene until the total volume of the filtered solution was 5 mL. The solution was carefully layered with 15 mL n-pentane and allowed to stand undisturbed for 3 days after which small, bright yellow, microcrystalline fibers had grown. The solution was cooled to −30° C. for 2 hr then filtered. The solids were rinsed once with n-pentane and briefly dried in vacuo. Yield: 351 mg (91%). Analytically pure material was obtained by an additional recrystallization from benzene/pentane. Crystals suitable for X-ray diffraction were obtained by layering a 5 mL of a non-saturated solution of 3 with 15 mL pentane. Thick brown needles were obtained after 3 days. $^1H$ NMR($C_6D_6$, 400 MHz): δ 7.30 (t, 12H, $P(C_6H_5)_3$), 7.14 (d, 4H, NAr—H), 7.00-6.86 (m, 18H, $P(C_6H_5)_3$), 6.77 (s, 4H, NAr—H). $^{31}P\{^1H\}$ NMR($C_6D_6$, 162 MHz): δ−2.80 (br). $^{19}F$ NMR($C_6D_6$, MHz): δ−128. $^{13}C\{^1H\}$ NMR($C_6D_6$, 100 MHz): δ 134.13 (d, $J_{PC}$=15.3 Hz), 133.79, 133.53, 129.92, 128.94 (d, $J_{PC}$=8.9 Hz), 120.92, 115.71 (d, $J_{PC}$=21.3 Hz). A satisfactory elemental analysis could not be obtained for 3, but the $^1H$, $^{31}P$, and $^{19}F$ NMR spectra of spectroscopically pure material is provided in FIG. 5.

Example 4

Synthesis of $(Ph_3P)_2Cu(carbazolate)$ (4)

A solution of triphenylphosphine (127.6 mg, 0.49 mmol, 2 eq.) in 3 mL benzene was added to a stirring suspension of $CuBr.SMe_2$ (50 mg, 0.24 mmol, 1 eq.) in 5 mL benzene, causing the suspended solids to dissolve. A suspension of Li(carbazolate).2.25 THF (81.6 mg, 0.24 mmol, 1 eq.) in 3 mL benzene was added dropwise to the stirring copper-phosphine mixture causing the causing solution to cloud and take a pale green-yellow color. The solution was stirred at ambient temperature overnight then concentrated to ca. 2 mL in vacuo. The concentrated solution was filtered through a glass microfiber filter with Celite. The filter was extracted with benzene until the total volume of the filtered solution was 5 mL. The solution was carefully layered with 15 ml n-pentane and allowed to stand undisturbed for 3 days after which large, colorless crystalline blocks suitable for X-ray diffraction had grown. The solids were filtered and rinsed once with n-pentane and briefly dried in vacuo. Yield: 121 mg (64%). $^1H$ NMR($C_6D_6$, 400 MHz): δ 8.52 (d, 2H, NAr—H), 7.67 ((d, 2H, NAr—H), 7.38 (t, 2H, NAr—H), 7.35-7.25 (m, 14H, NAr—H and $P(C_6H_5)_3$), 6.91 (t, 6H, $P(C_6H_5)_3$), 6.81 12H, $P(C_6H_5)_3$). $^{31}P\{^1H\}$ NMR($C_6D_6$, 162 MHz): 6-2.85 (br). $^{13}C\{^1H\}$ NMR($C_6D_6$, 100 MHz): δ 151.30, 134.13 (d, $J_{PC}$=15.1 Hz), 130.07, 129.04 ($J_{PC}$=9.0 Hz), 123.84, 120.53, 115.71, 115.09. Anal. calcd. for $C_{50}H_{44}CuNP_2C$, 76.56; H, 5.65; N, 1.79; Found: C, 76.23; H, 5.65; N, 1.89.

Testing and Measurement

The compounds prepared according to Examples 1 through 4 were subjected to the following testing and measurement procedures.

X-Ray Crystallography

X-ray quality crystals were grown as indicated in the experimental section for each compound. Single crystals were mounted on a glass fiber using Paratone-N oil. Low-temperature X-ray diffraction data were collected on a Siemens three-circle diffractometer coupled to a Bruker-ASX Smart Apex CCD detector with graphite monochromated Mo Kα radiation (λ=0.71073 Å). Structures were solved by direct methods using SHELXS and refined against $F^2$ on all data by full-matrix least squares with SHELXL-97. See, for example, Sheldrick, G. M. (1990) *Acta Cryst.* A46, 467-473; and Sheldrick, G. M. (2008) *Acta Cryst.* A64, 112-122, each of which is incorporated by reference in its entirety.

All non-hydrogen atoms were refined anisotropically. Hydrogen atoms were included at geometrically idealized positions and refined using a standard riding model. Structures were refined using established methods. See, for example, Müller, P. *Crystallography Reviews*, 2009, 15, 57-83, which is incorporated by reference in its entirety.

The diffraction data for $(PPh_3)_2Cu(NTol_2)$ (2) exhibited characteristic features of non-merohedral twinning and was refined accordingly: Two crystallographically independent domains with identical unit cell parameters were identified from the diffraction pattern using the Cell_Now software included in the SHELX package. See, for example, Müller, P.; Herbst-Irmer, R.; Spek, A. L.; Schneider, T. R.; Sawaya, M. R. *Crystal Structure Refinement: A Crystallographer's Guide to SHELXL*; Oxford University Press: New York, 2003; and Sheldrick, G. M. Cell_Now; University of Göttingen, Göttingen, Germany, each of which is incorporated by reference in its entirety. The domains were present in approximately a 60:40 ratio. The twinned nature of the crystal was taken into account in the .hkl file which employed the multi-domain HKL5 file format. At this point, the structure was refined by standard methods.

A single phenyl substituent of the diphenylamide ligand in $(PPh_3)_2Cu(NPh_2)$ (1) was disordered over two positions with 75:25 relative occupancy. The disorder was incorporated in the final model. FIGS. 2A-2D shows the displacement ellipsoid representations of copper compounds 1-4, respectively. Hydrogen atoms, solvent, and the minor component of the disorder were omitted for clarity.

Luminescence Lifetime Measurements

Solutions of analyte in MeCy were prepared in a nitrogen filled glovebox according to Table 1. Quartz fluorescence cuvettes (1 cm path length) were charged with analyte, fit with an air-tight silicone-lined screw cap and brought out of the glovebox. Luminescence measurements were determined by time-resolved phosphorescence spectroscopy as previously described. See, for example, Tomas, S. L.; Yagi, S.; Swager, T. M.; *J. Mater. Chem.* 2005, 15, 2829-2835, which is incorporated by reference in its entirety. The irradiation source was an Oriel nitrogen laser (Model 79111) with a 5 ns pulse width operating at approximately 3 Hz. The emitted light was dispersed in an Oriel MS-260i spectrograph with a 300 lines/mm grating and was detected by an Andor Technologies Intensified CCD camera (1024×128 pixels) with an onboard delay generator and a minimum gate width of 5 ns, operating in full vertical binning mode and triggered by a TTL pre-pulse from the nitrogen laser. The detector was calibrated using an Hg(Ar) pen lamp. Measurements were performed at ambient temperature. Measured values at each gate step position were accumulated from 15 pulses. All kinetic traces exhibited monoexponential decay and were fit to a first-order model. Decay constants for each sample were determined at three wavelengths at and around the emission maximum and averaged. The reported value is the average obtained from at least 3 samples.

TABLE 1

Data for Luminescence Lifetime Measurements.

| Compound | Concentration (M)[a] | $k_{obs}$ (μs$^{-1}$) | Lifetime (τ) (μs) |
|---|---|---|---|
| 1 | $1.3 \times 10^{-4}$ | 0.3206 | 3.1 |
|   | $6.6 \times 10^{-5}$ | 0.3152 | 3.2 |
|   | $3.3 \times 10^{-5}$ | 0.3116 | 3.2 |
|   |   |   | 3.15(5) (avg.) |
| 2 | $1.3 \times 10^{-4}$ | 0.3372 | 3.0 |
|   | $6.6 \times 10^{-5}$ | 0.3096 | 3.2 |
|   | $3.3 \times 10^{-5}$ | 0.3087 | 3.2 |
|   |   |   | 3.1(2) (avg.) |

TABLE 1-continued

Data for Luminescence Lifetime Measurements.

| Compound | Concentration (M)[a] | $k_{obs}$ (μs$^{-1}$) | Lifetime (τ) (μs) |
|---|---|---|---|
| 3[b] | 0.113 | 0.4022 | 2.5 |
|   | 0.024 | 0.3955 | 2.5 |
|   | 0.006 | 0.4085 | 2.4 |
|   | 0.014 | 0.3715 | 2.7 |
|   |   |   | 2.5(1) (avg.) |
| 4[c] | 0.063 | 0.0901 | 11.1 |
|   | 0.049 | 0.0801 | 12.3 |
|   | 0.032 | 0.0851 | 11.7 |
|   |   |   | 11.7(6) (avg.) |

[a]Approximate concentration.
[b]Due to low solubility in MeCy, concentrations cannot be reported. Instead the optical density at 400 nm is provided.
[c]Due to low solubility in MeCy, concentrations cannot be reported. Instead the optical density at 332 nm is provided.

Quantum Yield Measurements

In FIG. 8A-D, excitation and emission spectra for copper compounds 1-4 are shown. Emission spectra were collected on a SPEX Fluorolog-τ3 fluorimeter (Model FL-321, 450 W xenon lamp) using right angle detection. Two solutions of analyte in MeCy and one standard sample in benzene were prepared in a nitrogen filled glovebox and sealed in quartz fluorescence cuvettes (1 cm path length) equipped with an air-tight silicone-lined screw cap. The optical density of each sample was kept near or below 0.1 at the wavelength of excitation and beyond to minimize reabsorption of emitted light. Luminescence measurements were performed using 390 nm excitation at 298 K. Excitation monochromoter slits were adjusted to allow for a 3 nm resolution while the emission monochromoter slits were adjusted to allow for a 5 nm resolution. Optical spectra of the analyte solutions were obtained. Quantum yields were calculated from the measured quantities by the method of Demas and Crosby. See, for example Demas, J. N.; Crosby, G. A. *J. Phys. Chem.* 1971, 75, 991-1024, which has been incorporated by reference in its entirety. All quantum yields are reported in reference to a standard sample of perylene in benzene with an accepted quantum yield value of $\Phi_R = 0.99$. See, for example, Dawson, W. R.; Windsor, M. W. *J. Phys. Chem.* 1968, 72, 3251-3260, which is incorporated by reference in its entirety. The complete emission data is provided in Table 2.

TABLE 2

Data for Quantum Yield Measurements in MeCy at 298 K

| Compound | $\lambda_{ex}$ (nm) | O.D. at $\lambda_{ex}$ | I (counts)[a] | $\Phi$ (calc.)[b] |
|---|---|---|---|---|
| (perylene standard) | 390 | 0.065 | $9.958 \times 10^9$ |   |
| 1 |   | 0.100 | $4.441 \times 10^9$ | 0.26 |
| 1 |   | 0.113 | $5.031 \times 10^9$ | 0.26 |
| (perylene standard) | 390 | 0.027 | $6.644 \times 10^9$ |   |
| 1 |   | 0.069 | $3.495 \times 10^9$ | 0.18 |
| (perylene standard) | 390 | 0.041 | $1.446 \times 10^{10}$ |   |
| 2 |   | 0.132 | $1.137 \times 10^{10}$ | 0.23 |
| 2 |   | 0.069 | $6.319 \times 10^9$ | 0.22 |
| (perylene standard) | 390 | 0.028 | $6.773 \times 10^9$ |   |
| 3 |   | 0.097 | $3.043 \times 10^9$ | 0.12 |
| 3 |   | 0.136 | $4.038 \times 10^9$ | 0.11 |
| (perylene standard) | 390 | 0.100 | $1.022 \times 10^{10}$ |   |
| 3 |   | 0.009 | $1.916 \times 10^8$ | 0.18 |
| 3 |   | 0.019 | $2.431 \times 10^8$ | 0.11 |
| (perylene standard) | 390 | 0.010 | $2.889 \times 10^9$ |   |
| 4 |   | 0.009 | $6.335 \times 10^8$ | 0.22 |
| 4 |   | 0.016 | $1.432 \times 10^9$ | 0.27 |

[a]Integrated luminescence intensity.
[b]Uncertainty in quantum yield values is estimated at ±0.05.

Computational Details

DFT calculations were performed on $(PPh_3)_2Cu(N(p\text{-}FPH)_2)$ (3) using the Gaussian 03 program package. See, for example, Gaussian 03, Revision E.01, Frisch, M. J.; et al.; Gaussian, Inc., Wallingford Conn., 2004, which is incorporated by reference in its entirety. Molecular orbitals and energies were determined from a single-point calculation using the B3LYP hybrid functional and the 6-31+G* basis set. See, for example, Becke, A. D. *J. Chem. Phys.* 1993, 98, 5648-5652; Lee, C.; Yang, W.; Parr, R. G.; *Phys. Rev. B* 1988, 37, 785-789; V. A. Rassolov, M. A. Ratner, J. A. Pople, P. C. Redfern, and L. A. Curtiss, "6-31G* Basis Set for Third-Row Atoms," *J. Comp. Chem.*, 22 (2001) 976-84; V. A. Rassolov, J. A. Pople, M. A. Ratner, and T. L. Windus, "6-31G* basis set for atoms K through Zn," *J. Chem. Phys.*, 109 (1998) 1223-29; each of which is incorporated by reference in its entirety. Input coordinates were obtained from the X-ray structure.

Compound Decomposition and Impact on Photophysical Measurements

Samples of compounds 1-4 were observed to decompose upon dilution to concentrations below $1 \times 10^{-4}$ M in both benzene and MeCy despite preparation in a nitrogen-filled glove box using solvents that had been dried and degassed by the standard procedure described above. As the samples were diluted, progressive disappearance of low energy features in the optical spectrum was observed. Specifically a peak at ca. 335 nm and a shoulder at ca. 450 nm, features which appear prominently in the excitation spectra, were observed to lose intensity while a peak in the far-UV was observed to gain intensity. The solutions could also be seen to lose their yellow coloration and bright luminescence upon visual inspection. Sample decomposition was more pronounced in benzene than in methylcyclohexane, therefore all spectroscopic measurements were made in MeCy. These difficulties have made the collection of reliable absorption spectra impossible; however, excitation spectra are provided for each compound. No evidence of decomposition was observed in samples at concentrations typically used for $^1$H NMR spectroscopy.

Attempts were made to further exclude oxygen and water from analyte samples including degassing of solvents by three freeze-pump-thaw cycles, performing all sample preparations on a high-vacuum line, additional drying of benzene with a sodium-benzophenone-ketyl mixture followed by vacuum transferring directly into sample cuvettes, and additional drying of MeCy by stirring with tert-butyllithium for >12 h followed by vacuum transferring directly into sample cuvettes. These additional efforts made no discernable improvement on the integrity of dilute samples suggesting that neither water nor oxygen is responsible for the decomposition.

Luminescence lifetime measurements were carried out on a minimum of three samples whose concentrations spanned the range in which decomposition was observed (Table 1). The lifetimes were found to be constant throughout the measured range, suggesting that the decomposition products do not impact the measured values of $\tau$.

Unavoidably, the quantum yield measurements were carried out on partially decomposed sample. However, actions were taken to maximize the validity of the measurements. Analyte solutions for quantum yield determinations were prepared as concentrated as possible to minimize decomposition and an excitation wavelength was selected ($\lambda_{ex}$=390 nm) where the decomposed material did not have a significant absorbance such that the measured optical density was largely due to the desired compound. As a result, experimental quantum yield values were acceptably reproducible, but likely represent lower limits.

Results 1-4 were thermally stable but were highly sensitive to adventitious oxygen and water and discolored rapidly in aerated solution giving insoluble brown solids with concomitant loss of luminescence. The compounds were relatively robust in the solid state. Powdered material retained both color and bright luminescence after several weeks at ambient conditions.

In FIG. 2A-2D, the solid state structures of 1-4 shown were determined by single-crystal X-ray diffraction and revealed monomeric compounds in which the amide ligand adopted a monodentate coordination mode. Examples of monomeric copper compounds with terminal amide ligands, whether luminescent or not, are exceedingly rare and have only been reported recently. See, for example, Blue, E. D.; Davis, A.; Conner, D.; Gunnoe, T. B.; Boyle, P. D.; White, P. S. *J. Am. Chem. Soc.* 2003, 125, 9435-9441; Goj, L. A.; Blue, E. D.; Munro-Leighton, C.; Gunnoe, T. B.; Petersen, J. L. *Inorg. Chem.*, 2005, 44, 8647-8649; Reiє, P.; Fenske, D. Z. *Anorg. Allg. Chem.* 2000, 626, 1317-1331; and Mankad, N. P.; Antholine, W. E.; Szilagyi, R. K.; Peters, J. C. *J. Am. Chem. Soc.* 2009, 131, 3878-3880, each of which is incorporated by reference in its entirety. Each compound exhibited a three-coordinate metal center with nearly ideal trigonal planar geometry; 1-4 were rigorously planar as indicated by the angles about copper which sum to 360.00° within experimental error, while in all cases the P—Cu—P, and N—Cu—P bond angles were within 10° of the ideal value of 120°. The amide ligand exhibited a large C—N—Cu—P dihedral angle suggesting little to no contribution of an $N(\pi) \rightarrow Cu(4p)$ interaction to the copper-amide bonding. The Cu—N internuclear distances ranged from 1.9363(17) (2) to 1.9602(16) Å (1) which fall between the few structurally characterized examples. Variation of the substituent in the amido ligand in the series 1-3 had no apparent structural impact.

Figure 5:
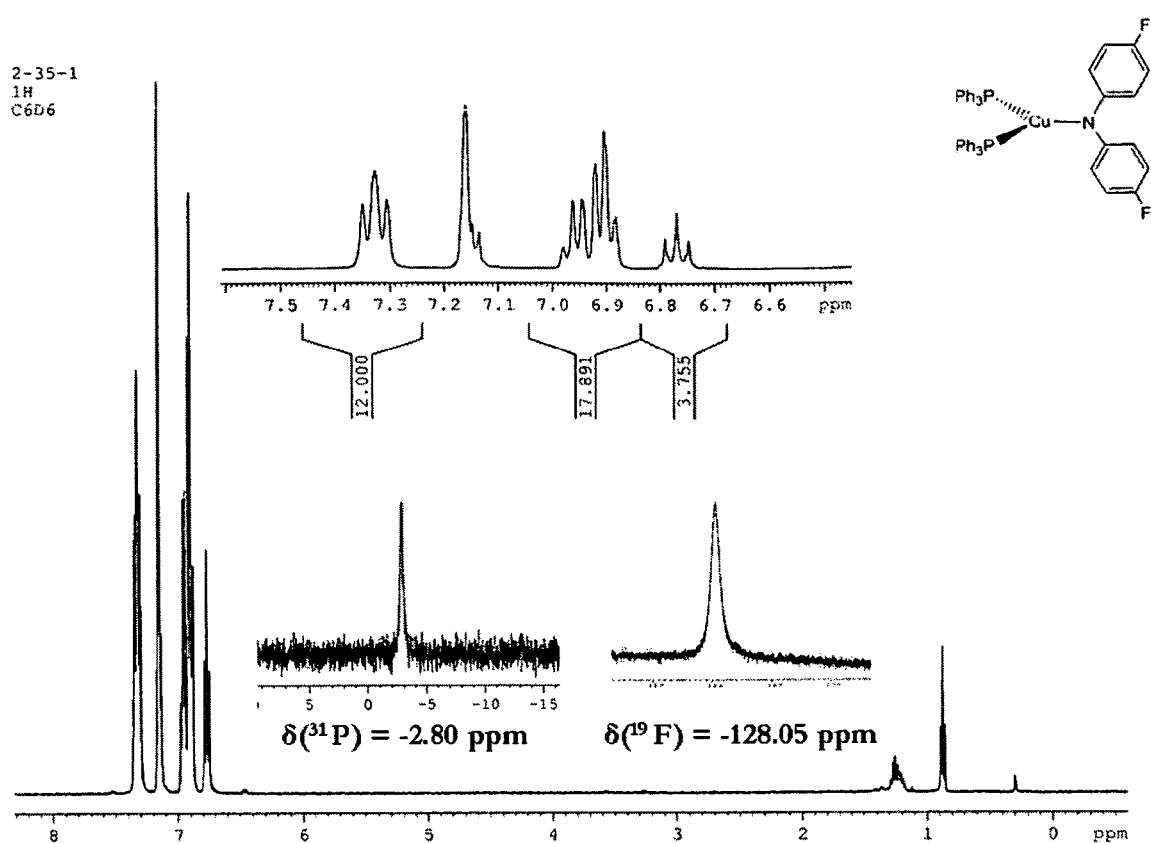
FIG. 5 is a depiction of $^1H$, $^{31}P$, and $^{19}F$ NMR spectra of $(Ph_3P)_2Cu(N(\rho\text{-}FPH)_2)$.

1-4 exhibited pseudo-$C_2$ symmetry in the solid state, with the two-fold axis coincident with the Cu—N vector. In FIG. 5, $^1$H and $^{31}$P NMR measurements which showed a single phosphorous resonance and equivalent protons on the amide ligands, where expected, demonstrate that $C_2$ symmetry was preserved in benzene solution at room temperature.

Figure 3:
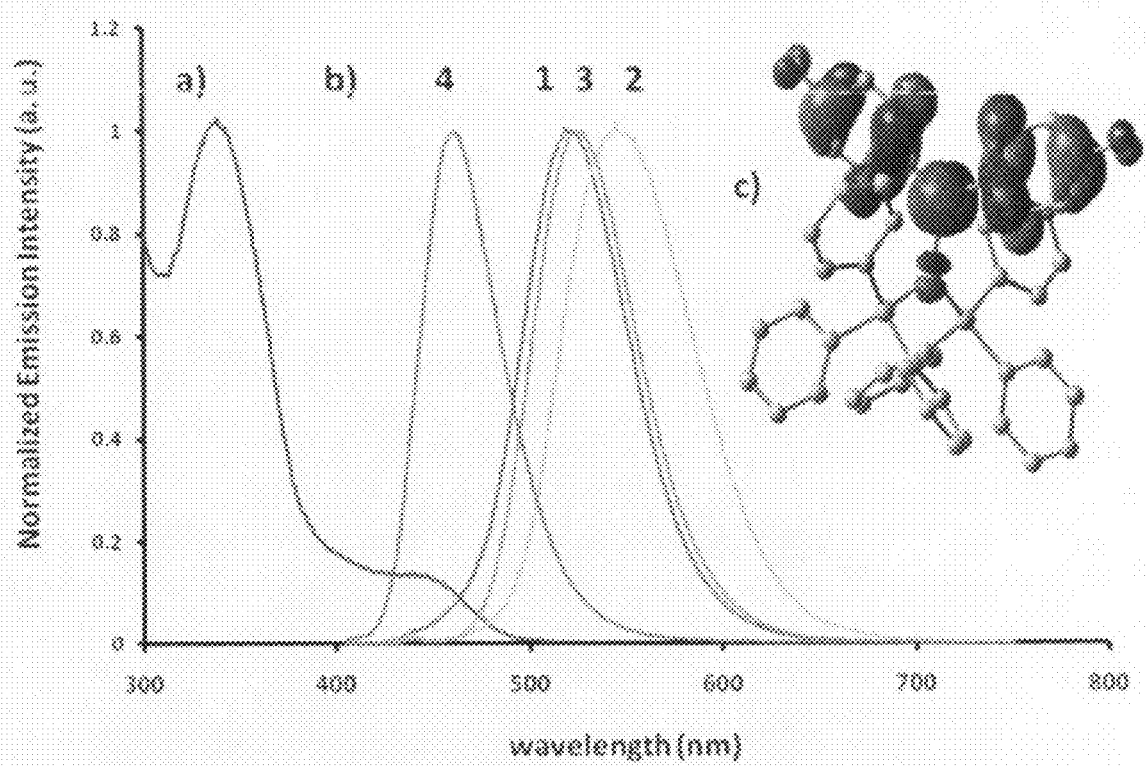
FIG. 3 includes (a) an excitation spectrum of copper compound 1 in MeCy at room temperature; (b) emission spectra of copper compounds 1-4 in MeCy at room temperature; and (c) highest occupied molecular orbital (HOMO) of copper compound 3, calculated by Density Functional Theory (DFT) (isovalue=0.03).

1-4 exhibited bright luminescence both in the solid state and in methylcyclohexane (MeCy) solution at room temperature. In FIG. 3B, the parent diphenylamide compound (1) exhibited green luminescence, centered at 521 nm. Substitution with fluorine at the para position on the amide phenyl rings (3) resulted in a negligible bathochromic shift in $\lambda_{em}$ while functionalization with methyl groups (2) shifted the emission by 25 nm to longer wavelength. Copper carbazolate 4 exhibited blue emission centered at 461 nm suggestive of a different electronic structure from 1-3.

Solution quantum yields were determined by comparison of the integrated emission intensity to a standard sample of perylene and excited-state lifetimes were determined by time-resolved emission spectroscopy. 1, 2, and 4 were comparably efficient emitters, with Φ varying over the narrow range 0.22-0.24. In FIG. 9A-D, each compound exhibited a monoexponential luminescence decay profile in solution with lifetimes on the microsecond timescale, suggesting a phosphorescence process. The lifetimes for the isostructural series 1-3 showed little alteration upon substitution of the amide ligand while exchange of the diphenylamide for the more rigid carbazolate ligand resulted in a four-fold enhancement of the lifetime. While 1-4 were less efficient than copper amidophosphine compounds, they represent a substantial improvement in quantum yield and luminescence lifetime over the copper diimine compounds that are the most extensively studied class of copper emitters to date. See, for example, Cline, E. D.; Kraml, C. M.; Byrne, N.; Ho, D. M.; Qin, Q.; Coughlin, F. J.; Bernhard, S.; Pascal, R. A. *Inorg. Chem.* 2008, 47, 10378-10388. Goldsmith, J. I.; Hudson, W. R.; Lowry, M. S.; Anderson, T. H.; Berhard, S. *J. Am. Chem. Soc.* 2005, 127, 7502-7510; Ford, P. C.; Cariati, E.; Bourassa, J. *Chem. Rev.* 1999, 99, 3625-3627; Horvath, O. *Coord. Chem. Rev.* 1994, 135/136, 303-324; Balzani, V.; Juris, A.; Venturi, M.; Campagna, S.; Serroni, S. *Chem. Rev.* 1996, 96, 759-833; Zolo, R. F.; Lipton, S.; Dori, Z. *Chem. Comm.* 1970, 1124-1125; Kutal, C. *Coord. Chem. Rev.* 1990, 99, 213-252; Robertson, N. *Chem. Sus. Chem.* 2008, 1, 977-979; McMillin, D. R.; McNett, K. M. *Chem. Rev.* 1998, 98, 1201-1219; Cuttell, D. G.; Kuang, S.-M.; Fanwick, P. E.; McMillin, D. R.; Walton, R. A. *J. Am. Chem. Soc.* 2002, 124, 6-7; James, A. M.; Laxman, R. K.; Fronczek, F. R.; Maverick, A. W. *Inorg. Chem.* 1998, 37, 3785-3791; and Noto, M.; Goto, Y.; Era, M. *Chem. Lett.* 2003, 32, 32-33, each of which is incorporated by reference in its entirety. The photophysical properties of copper compounds are shown in Table 3.

TABLE 3

Photophysical properties of copper compounds at room temperature in methylcyclohexane.

| compound | λem (nm) | Φema, b | τem (μs) c |
|---|---|---|---|
| 1 | 521 | 0.23 | 3.17(5) |
| 2 | 546 | 0.22 | 3.1(2) |
| 3 | 525 | 0.13 | 2.5(1) |
| 4 | 461 | 0.24 | 11.7(6) | a. uncertainty in quantum yield measurements is estimated to be ±0.05.
b. $\lambda_{ex}$ = 390 nm.
c. $\lambda_{ex}$ = 337 nm The electronic structure of 3 was explored using Density Functional Theory (DFT) calculations at the B3LYP/6-31+G* level of theory. As illustrated in FIG. 3C, the computed highest occupied molecular orbital (HOMO) was localized primarily on the diphenylamide ligand with substantial nitrogen pπ, C—C π, and fluorine pπ character. There was only a small contribution from a Cu d-orbital. The HOMO was nearly identical to those calculated for a related class of compounds. See, for example, Ford, P. C.; Cariati, E.; Bourassa, J. *Chem. Rev.* 1999, 99, 3625-3627; Horvath, O. *Coord. Chem. Rev.* 1994, 135/136, 303-324; Balzani, V.; Juris, A.; Venturi, M.; Campagna, S.; Serroni, S. *Chem. Rev.* 1996, 96, 759-833; Zolo, R. F.; Lipton, S.; Dori, Z. *Chem. Comm.* 1970, 1124-1125; Kutal, C. *Coord. Chem. Rev.* 1990, 99, 213-252; Robertson, N. *Chem. Sus. Chem.* 2008, 1, 977-979; McMillin, D. R.; McNett, K. M. *Chem. Rev.* 1998, 98, 1201-1219; Cuttell, D. G.; Kuang, S.-M.; Fanwick, P. E.; McMillin, D. R.; Walton, R. A. *J. Am. Chem. Soc.* 2002, 124, 6-7; James, A. M.; Laxman, R. K.; Fronczek, F. R.; Maverick, A. W. *Inorg. Chem.* 1998, 37, 3785-3791; and Noto, M.; Goto, Y.; Era, M. *Chem. Lett.* 2003, 32, 32-33, each of which is incorporated by reference in its entirety. The calculated lowest unoccupied molecular orbital (LUMO) had exclusively $PPh_3$ aryl π parentage, however, the high density of ligand-based orbitals of similar energy to the LUMO rendered the validity of this result questionable. While the detailed photophysics of these and related copper amidophosphine compounds are not known, computational results in addition to X-ray absorption studies on related systems strongly suggest that ligand centered states play an important role. See, for example, Mankad, N. P.; Antholine, W. E.; Szilagyi, R. K.; Peters, J. C. *J. Am. Chem. Soc.* 2009, 131, 3878-3880; and Harkins, S. B.; Mankad, N. P.; Miller, A. J. M.; Szilagyi, R. K.; Peters, J. C. *J. Am. Chem. Soc.* 2008, 130, 3478-3485, each of which is incorporated in its entirety. Specifically, initial excitation may involve charge transfer from the amido nitrogen generating an aminyl radical species.

A device including a compound, exemplified in FIG. 10, includes an excitation source 20 configured to excite a compound 30, which in turn can emit light. The excitation source can be a lamp, laser, or other light source, or a voltage source configured to apply a potential, or change in voltage, across a region including the compound. The potential or change in voltage across the region can excite the compound leading to emission of light.

Other embodiments are within the scope of the following claims.

What is claimed is:
1. A compound represented by Formula II:

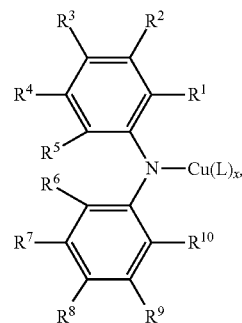

wherein:
L is $Z(R^c)_3$ or has the formula:

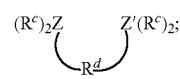

Z is P, and Z', if present, is P;
$R^d$ is a group selected from an optionally substituted alkylene group optionally interrupted by O, S or $NR^b$, an optionally substituted arylene group, an optionally substituted heteroarylene group, an optionally substituted arylalkylene group, and an optionally substituted heteroarylalkylene group;
x is 1 or 2;
each of $R^1$ through $R^{10}$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and
each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.
2. The compound of claim 1, wherein the compound is $(Ph_3P)_2Cu(NPh_2)$, $(Ph_3P)_2Cu(NTol_2)$, or $(Ph_3P)_2Cu(N(p-FPh)_2)$.

3. A monomeric metal compound represented by Formula I:

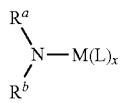

wherein:
L has the formula

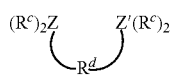

x is 1; and
Z and Z' are each independently P;
each $R^c$, independently, is a group selected from hydrogen, an optionally substituted alkyl group, an optionally substituted alkenyl group, an optionally substituted alkynyl group, an optionally substituted aryl group, and an optionally substituted heteroaryl group;
$R^d$ is a group selected from an optionally substituted alkylene group optionally interrupted by O, S or $NR^b$, an optionally substituted arylene group, an optionally substituted heteroarylene group, an optionally substituted arylalkylene group, and an optionally substituted heteroarylalkylene group;
M is Cu, Ag, Au, Zn, Cd or Hg; and
$R^a$ is an optionally substituted aryl group;
$R^b$ is an optionally substituted alkyl group, an optionally substituted alkenyl group, an optionally substituted alkynyl group, an optionally substituted aryl group, or an optionally substituted heteroaryl group; or
$R^a$ and $R^b$ and N together form an aryl group.

4. The compound of claim 3, wherein the compound is represented by Formula III:

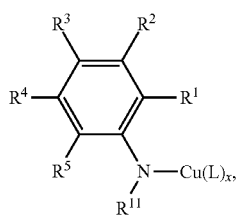

wherein:
Z is P, and Z' is P;
each of $R^1$ through $R^5$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group;
$R^{11}$ is selected from the group consisting of hydrogen, an acyl group, an optionally substituted alkyl group, an optionally substituted alkenyl group, an optionally substituted alkynyl group, an optionally substituted aryl group, and an optionally substituted heteroaryl group; and each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

5. The compound of claim 3, wherein the compound is represented by Formula IV:

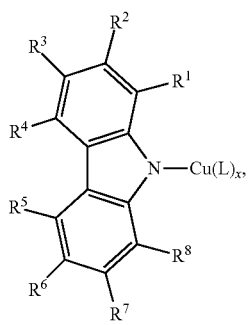

wherein:
Z is P, and Z' is P;
each of $R^1$ through $R^8$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and
each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

6. The compound of claim 3, wherein the compound is represented by Formula V:

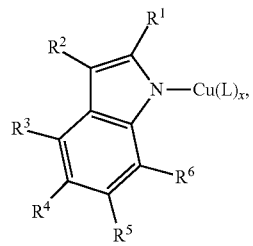

wherein:
Z is P, and Z' is P;
each of $R^1$ through $R^6$ independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and
each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

7. The compound of claim 3, wherein L is a bisphosphinoalkane family ligand, a BISBI family ligand, a DPPF family ligand, a XANTphos family ligand, or a BINAP family ligand.

8. A luminescent device including a compound represented by Formula II:

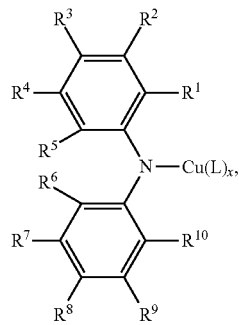

wherein:

L is $Z(R^c)_3$ or has the formula:

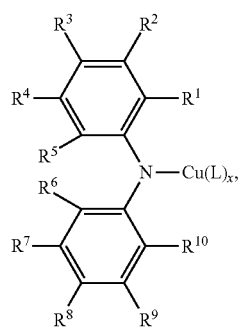

Z is P, and Z', if present, is P;

$R^d$ is a group selected from an optionally substituted alkylene group optionally interrupted by O, S or $NR^b$, an optionally substituted arylene group, an optionally substituted heteroarylene group, an optionally substituted arylalkylene group, and an optionally substituted heteroarylalkylene group;

x is 1 or 2;

each of $R^1$ through $R^{10}$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

9. The device of claim 8, wherein the compound is $(Ph_3P)_2Cu(NPh_2)$, $(Ph_3P)_2Cu(NTol_2)$, or $(Ph_3P)_2Cu(N(\rho\text{-}FPh)_2)$.

10. A luminescent device including a compound represented by Formula I:

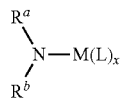

wherein:

L has the formula

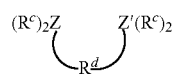

x is 1; and

Z and Z' are each independently P;

each $R^c$, independently, is a group selected from hydrogen, an optionally substituted alkyl group, an optionally substituted alkenyl group, an optionally substituted alkynyl group, an optionally substituted aryl group, and an optionally substituted heteroaryl group;

$R^d$ is a group selected from an optionally substituted alkylene group optionally interrupted by O, S or $NR^b$, an optionally substituted arylene group, an optionally substituted heteroarylene group, an optionally substituted arylalkylene group, and an optionally substituted heteroarylalkylene group;

M is Cu, Ag, Au, Zn, Cd or Hg; and $R^a$ is an optionally substituted aryl group;

$R^b$ is an optionally substituted alkyl group, an optionally substituted alkenyl group, an optionally substituted alkynyl group, an optionally substituted aryl group, or an optionally substituted heteroaryl group; or $R^a$ and $R^b$ and N together form an aryl group.

11. The device of claim 10, wherein the compound is represented by Formula III:

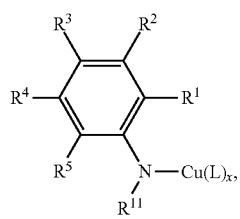

wherein:

Z is P, and Z' is P;

each of $R^1$ through $R^5$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group;

$R^{11}$ is selected from the group consisting of hydrogen, an acyl group, an optionally substituted alkyl group, an optionally substituted alkenyl group, an optionally substituted alkynyl group, an optionally substituted aryl group, and an optionally substituted heteroaryl group; and each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

12. The device of claim 10, wherein the compound is represented by Formula IV:

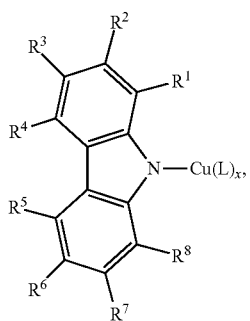

IV wherein:
Z is P, and Z' is P;
each of $R^1$ through $R^8$, independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and
each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

13. The device of claim 10, wherein the compound is represented by Formula V:

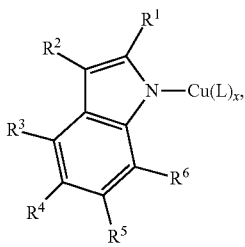

V wherein:
Z is P, and Z' is P;
each of $R^1$ through $R^6$ independently, is selected from the group consisting of hydrogen, a halogen, hydroxyl, cyano, nitro, di(alkyl)amino, an alkoxy group, an acyl group, an optionally substituted alkyl group, an optionally substituted alkenyl group, an optionally substituted alkynyl group, an optionally substituted aryl group, and an optionally substituted heteroaryl group; and
each $R^c$, independently, is selected from the group consisting of hydrogen, an optionally substituted alkyl group, an optionally substituted alkenyl group, an optionally substituted alkynyl group, an optionally substituted aryl group, and an optionally substituted heteroaryl group.

14. The device of claim 10, wherein L is a bisphosphinoalkane family ligand, a BISBI family ligand, a DPPF family ligand, a XANTphos family ligand, or a BINAP family ligand.

15. The device of claim 10, further comprising an electric power source configured to electrically excite the compound.

16. A method of generating light comprising:
exciting a compound represented by Formula I

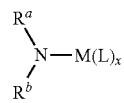

I wherein:
L has the formula:

$(R^c)_2Z \underset{R^d}{\frown} Z'(R^c)_2$;

Z and Z' are each independently P;
each $R^c$, independently, is a group selected from hydrogen, an optionally substituted alkyl group, an optionally substituted alkenyl group, an optionally substituted alkynyl group, an optionally substituted aryl group, and an optionally substituted heteroaryl group;
$R^d$ is a group selected from an optionally substituted alkylene group, an optionally substituted arylene group, an optionally substituted heteroarylene group, an optionally substituted arylalkylene group, and an optionally substituted heteroarylalkylene group;
x is 1;
M is Cu, Ag, Au, Zn, Cd or Hg; and
$R^a$ is an optionally substituted aryl group;
$R^b$ is an optionally substituted alkyl group, an optionally substituted alkenyl group, an optionally substituted alkynyl group, an optionally substituted aryl group, or an optionally substituted heteroaryl group; or
$R^a$ and $R^b$ and N together form an aryl group.

17. The method of claim 16, wherein exciting the compound includes photoexcitation or electrical excitation.

* * * * *